US006900046B2

(12) United States Patent
Donoho et al.

(10) Patent No.: US 6,900,046 B2
(45) **Date of Patent: *May 31, 2005**

(54) HUMAN ATPASE PROTEINS AND POLYNUCLEOTIDES ENCODING THE SAME

(75) Inventors: Gregory Donoho, The Woodlands, TX (US); C. Alexander Turner, Jr., The Woodlands, TX (US); Erin Hilbun, Spring, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/231,354

(22) Filed: Aug. 28, 2002

(65) Prior Publication Data

US 2003/0023065 A1 Jan. 30, 2003

Related U.S. Application Data

(63) Continuation of application No. 09/710,092, filed on Nov. 10, 2000, now Pat. No. 6,462,186.
(60) Provisional application No. 60/164,624, filed on Nov. 10, 1999.

(51) Int. Cl.$^7$ .......................... C12N 1/20; C12N 15/00; C12N 9/26; C07H 21/04
(52) U.S. Cl. ................. 435/252.3; 435/201; 435/320.1; 536/23.2
(58) Field of Search ........................... 435/252.3, 320.1, 435/201, 325, 440; 536/23.2, 23.1; 514/44; 424/450

(56) References Cited

U.S. PATENT DOCUMENTS

| | | | | |
|---|---|---|---|---|
| 4,215,051 | A | | 7/1980 | Schroeder et al. |
| 4,376,110 | A | | 3/1983 | David et al. |
| 4,946,778 | A | | 8/1990 | Ladner et al. |
| 5,759,795 | A | | 6/1998 | Jubin |
| 5,783,566 | A | * | 7/1998 | Mislick ....................... 514/44 |
| 5,837,458 | A | | 11/1998 | Minshull et al. |
| 5,869,336 | A | | 2/1999 | Meyer et al. |
| 5,877,397 | A | | 3/1999 | Lonberg et al. |
| 5,932,444 | A | | 8/1999 | Hillman et al. |
| 6,010,852 | A | | 1/2000 | Hillman et al. |
| 6,075,181 | A | | 6/2000 | Kucherlapati et al. |

FOREIGN PATENT DOCUMENTS

WO WO 00 58473 A 10/2000

OTHER PUBLICATIONS

Strausberg. NCBI AA55806. 1997.*

Sequence Alignment of SEQ ID No:13.*

EMBL Database, Heidelberg, FRG accesion No. AW024552, Sep. 14, 1999, NCI–CGAP: "wu77c05.x1 NCI_CGAP_Kid 3 *Homo sapiens* cDNA clone image: 252056 3' similar to WP: WO9D10.2 CE16563 ATPASE, mRNA sequence" XP002165685.

Halleck, M.S. et al., 1998, "Multiple Members of a Third Subfamily of P–Type ATPases Identified by Genomic Sequences and ESTs", Genome Research 8(4): 354–361. XP002132690, Accession No.: AF011337.

Nagase, T. et al, 2000, "Pedicition of the Coding Sequences of Unidentified Human Genes. XVII. The Complete Sequences of 100 New cDNA Clones from Brain Which Code for Large Proteins in vitro", DNA Research 7(2):143–150. XP000983090, clone XP00983090.

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

(Continued)

*Primary Examiner*—Ponnathapua Chutamurthy
*Assistant Examiner*—Yong D. Pak

(57) ABSTRACT

Novel human polynucleotide and polypeptide sequences are disclosed that can be used in therapeutic, diagnostic, and pharmacogenomic applications.

6 Claims, No Drawings

OTHER PUBLICATIONS

Janknecht et al, 1991, "Rapid and efficient purification of native histidine–tagged protein expressed by recombinant vaccinia virus", PNAS USA 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1980, "Transformation of mammalian cells with an amplifiable dominant–acting gene", Proc. Natl. Acad. Sci. USA 77(6):3567–3570.

Wigler et al, 1977, "Transfer of Purified Herpes Virus Thymidine Kinase Gene to Cultured Mouse Cell", Cell 11:223–232.

* cited by examiner

HUMAN ATPASE PROTEINS AND POLYNUCLEOTIDES ENCODING THE SAME

The present application is a continuation of co-pending U.S. application Ser. No. 09/710,092 filed on Nov. 10, 2000, now U.S. Pat. No. 6,462,186 which claims the benefit of U.S. Provisional Application Ser. No. 60/164,624, which was filed on Nov. 10, 1999, and is herein incorporated by reference in its entirety.

1. INTRODUCTION

The present invention relates to the discovery, identification, and characterization of novel human polynucleotides encoding proteins that share sequence similarity with animal ATPase proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring and the treatment of diseases and disorders.

2. BACKGROUND OF THE INVENTION

ATPases are proteins that mediate, facilitate, or "power" a wide variety of chemical processes within the cell. For example, ATPases have been associated with enzymatic, catabolic, and metabolic processes as well as transport mechanisms, blood coagulation, phagocytosis, etc.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal ATPases.

The novel human nucleic acid sequences described herein, encode alternative proteins/open reading frames (ORFs) of 972, 124, 1,056, 208, 1,270, 422, 1,426, and 578 amino acids in length (see SEQ ID NOS: 2, 4, 6, 8, 10, 12, 14, and 16 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP genes (e.g., expression constructs that place the described gene under the control of a strong promoter system), and transgenic animals that express a NHP transgene, or "knock-outs" (which can be conditional) that do not express a functional NHP. A knockout ES cell line has been produced that contains a gene trap mutation in the murine ortholog of the described locus.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences. SEQ ID NO:17 describes a NHP ORF as well as flanking 5' and 3' sequences.

5. DETAILED DESCRIPTION OF THE INVENTION

The NHPs, described for the first time herein, are novel proteins that are expressed in, inter alia, human cell lines, predominantly in human kidney and placenta, as well as human fetal brain, brain, pituitary, cerebellum, spinal cord, thymus, spleen, lymph node, bone marrow, trachea, fetal liver, prostate, testis, thyroid, adrenal gland, salivary gland, stomach, small intestine, colon, uterus, mammary gland, adipose, esophagus, bladder, cervix, rectum, ovary, fetal kidney, fetal lung and gene trapped human cells.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length can partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or “wobble” oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be “tailed” using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, “Antibodies: A Laboratory Manual”, Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding the NHPs, NHP fusion protein products (especially NHP-Ig fusion proteins, i.e., fusions of a NHP,.or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and the corresponding deduced amino acid sequences of the described NHPs are presented in the Sequence Listing. The NHP nucleotides were obtained from clustered human gene trapped sequences, ESTs and a human placenta cDNA library (Edge Biosystems, Gaithersburg, Md.). The described sequences share structural similarity with calcium transporting ATPases and aminophospholipid transporters.

5.2 NHPS AND NHP POLYPEPTIDES

NHPs, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease. Given the similarity information and expression data, the described NHPs can be targeted (by drugs, oligos, antibodies, etc,) in order to treat disease, or to therapeutically augment the efficacy of therapeutic agents.

The Sequence Listing discloses the amino acid sequences encoded by the described NHP genes. The NHPs typically display initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, transport, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising the nucleic acid sequence described in SEQ ID NO: 13.

2. The recombinant expression vector of claim 1, wherein said vector comprises a nucleic acid sequence that encodes the amino acid sequence of SEQ ID NO 14.

3. A host cell comprising the vector of claim 1.

4. A gene delivery system comprising an isolated nucleic acid molecule comprising the nucleic acid sequence described in SEQ ID NO:13.

5. The gene delivery system of claim 4, wherein said isolated nucleic acid molecule is present in a viral vector.

6. The gene delivery system of claim 4, wherein said isolated nucleic acid molecule is present in a cationic lipid complex.

* * * * *

SEQUENCE LISTING

<160> NUMBER OF SEQ ID NOS: 17

<210> SEQ ID NO 1
<211> LENGTH: 2919
<212> TYPE: DNA
<213> ORGANISM: homo sapiens

<400> SEQUENCE: 1

```
atgactgagg ctctccaatg ggccagatat cactggcgac ggctgatcag aggtgcaacc     60

agggatgatg attcagggcc atacaactat tcctcgttgc tcgcctgtgg gcgcaagtcc    120

tctcagatcc ctaaactgtc aggaaggcac cggattgttg ttccccacat ccagcccttc    180

aaggatgagt atgagaagtt ctccggagcc tatgtgaaca atcgaatacg aacaacaaag    240

tacacacttc tgaattttgt gccaagaaat ttatttgaac aatttcacag agctgccaat    300

ttatatttcc tgttcctagt tgtcctgaac tgggtacctt tggtagaagc cttccaaaag    360

gaaatcacca tgttgcctct ggtggtggtc cttacaatta tcgcaattaa agatggcctg    420

gaagattatc ggaaatacaa aattgacaaa cagatcaata atttaataac taaagtttat    480

agtaggaaag agaaaaaata cattgaccga tgctggaaag acgttactgt tggggacttt    540

attcgcctct cctgcaacga ggtcatccct gcagacatgg tactactctt ttccactgat    600

ccagatggaa tctgtcacat tgagacttct ggtcttgatg gagagagcaa tttaaaacag    660

aggcaggtgg ttcggggata tgcagaacag gactctgaag ttgatcctga gaagttttcc    720

agtaggatag aatgtgaaag cccaaacaat gacctcagca gattccgagg cttcctagaa    780

cattccaaca aagaacgcgt gggtctcagt aaagaaaatt tgttgcttag aggatgcacc    840

attagaaaca cagaggctgt tgtgggcatt gtggtttatg caggccatga aaccaaagca    900

atgctgaaca acagtgggcc acggtataag cgcagcaaat tagaaagaag agcaaacaca    960

gatgtcctct ggtgtgtcat gcttctggtc ataatgtgct taactggcgc agtaggtcat   1020

ggaatctggc tgagcaggta tgaaaagatg cattttttca atgttcccga gcctgatgga   1080

catatcatat caccactgtt ggcaggattt tatatgtttt ggaccatgat cattttgtta   1140

caggtcttga ttcctatttc tctctatgtt tccatcgaaa ttgtgaagct tggacaaata   1200

tatttcattc aaagtgatgt ggatttctac aatgaaaaaa tggattctat tgttcagtgc   1260

cgagccctga acatcgccga ggatctggga cagattcagt acctcttttc cgataagaca   1320

ggaaccctca ctgagaataa gatggttttt cgaagatgta gtgtggcagg atttgattac   1380

tgccatgaag aaaatgccag gaggttggag tcctatcagg aagctgtctc tgaagatgaa   1440

gattttatag acacagtcag tggttccctc agcaatatgg caaaaccgag agcccccagc   1500

tgcaggacag ttcataatgg gcctttggga aataagccct caaatcatct tgctgggagc   1560

tcttttactc taggaagtgg agaaggagcc agtgaagtgc ctcattccag acaggctgct   1620

ttcagtagcc ccattgaaac agacgtggta ccagacacca ggcttttaga caaatttagt   1680

cagattacac ctcggctctt tatgccacta gatgagacca tccaaaatcc accaatggaa   1740

actttgtaca ttatcgactt tttcattgca ttggcaattt gcaacacagt agtggtttct   1800

gctcctaacc aaccccgaca aaagatcaga caccccttcac tgggggggtt gcccattaag   1860

tctttggaag agattaaaag tcttttccag agatggtctg tccgaagatc aagttctcca   1920

tcgcttaaca gtgggaaaga gccatcttct ggagttccaa acgcctttgt gagcagactc   1980

cctctcttta gtcgaatgaa accagcttca cctgtggagg aagaggtctc ccaggtgtgt   2040
```

-continued

```
gagagccccc agtgctccag tagctcagct tgctgcacag aaacagagaa acaacacggt   2100

gatgcaggcc tcctgaatgg caaggcagag tccctccctg gacagccatt ggcctgcaac   2160

ctgtgttatg aggccgagag cccagacgaa gcggccttag tgtatgccgc cagggcttac   2220

caatgcactt tacggtctcg gacaccagag caggtcatgg tggactttgc tgctttggga   2280

ccattaacat ttcaactcct acacatcctg ccctttgact cagtaagaaa aagaatgtct   2340

gttgtggtcc gacaccctct ttccaatcaa gttgtggtgt atacgaaagg cgctgattct   2400

gtgatcatgg agttactgtc ggtggcttcc ccagatggag caagtctgga gaaacaacag   2460

atgatagtaa gggagaaaac ccagaagcac ttggatgact atgccaaaca aggccttcgt   2520

actttatgta tagcaaagaa ggtcatgagt gacactgaat atgcagagtg gctgaggaat   2580

cattttttag ctgaaaccag cattgacaac agggaagaat tactacttga atctgccatg   2640

aggttggaga acaaacttac attacttggt gctactggca ttgaagaccg tctgcaggag   2700

ggagtccctg aatctataga agctcttcac aaagcgggca tcaagatctg gatgctgaca   2760

ggggacaagc aggagacagc tgtcaacata gcttatgcat gcaaactact ggagccagat   2820

gacaagcttt ttatcctcaa tacccaaagt aaagtgcgta tattgagatt aaatctgttc   2880

ttctgtattt tcaaaggcat tggaacattt gagatttga                           2919


<210> SEQ ID NO 2
<211> LENGTH: 972
<212> TYPE: PRT
<213> ORGANISM: homo sapiens

<400> SEQUENCE: 2

Met Thr Glu Ala Leu Gln Trp Ala Arg Tyr His Trp Arg Arg Leu Ile
 1               5                  10                  15

Arg Gly Ala Thr Arg Asp Asp Asp Ser Gly Pro Tyr Asn Tyr Ser Ser
            20                  25                  30

Leu Leu Ala Cys Gly Arg Lys Ser Ser Gln Ile Pro Lys Leu Ser Gly
        35                  40                  45

Arg His Arg Ile Val Val Pro His Ile Gln Pro Phe Lys Asp Glu Tyr
    50                  55                  60

Glu Lys Phe Ser Gly Ala Tyr Val Asn Asn Arg Ile Arg Thr Thr Lys
65                  70                  75                  80

Tyr Thr Leu Leu Asn Phe Val Pro Arg Asn Leu Phe Glu Gln Phe His
                85                  90                  95

Arg Ala Ala Asn Leu Tyr Phe Leu Phe Leu Val Val Leu Asn Trp Val
            100                 105                 110

Pro Leu Val Glu Ala Phe Gln Lys Glu Ile Thr Met Leu Pro Leu Val
        115                 120                 125

Val Val Leu Thr Ile Ile Ala Ile Lys Asp Gly Leu Glu Asp Tyr Arg
    130                 135                 140

Lys Tyr Lys Ile Asp Lys Gln Ile Asn Asn Leu Ile Thr Lys Val Tyr
145                 150                 155                 160

Ser Arg Lys Glu Lys Lys Tyr Ile Asp Arg Cys Trp Lys Asp Val Thr
                165                 170                 175

Val Gly Asp Phe Ile Arg Leu Ser Cys Asn Glu Val Ile Pro Ala Asp
            180                 185                 190

Met Val Leu Leu Phe Ser Thr Asp Pro Asp Gly Ile Cys His Ile Glu
        195                 200                 205

Thr Ser Gly Leu Asp Gly Glu Ser Asn Leu Lys Gln Arg Gln Val Val
    210                 215                 220
```

-continued

```
Arg Gly Tyr Ala Glu Gln Asp Ser Glu Val Asp Pro Glu Lys Phe Ser
225                 230                 235                 240

Ser Arg Ile Glu Cys Glu Ser Pro Asn Asn Asp Leu Ser Arg Phe Arg
                245                 250                 255

Gly Phe Leu Glu His Ser Asn Lys Glu Arg Val Gly Leu Ser Lys Glu
            260                 265                 270

Asn Leu Leu Leu Arg Gly Cys Thr Ile Arg Asn Thr Glu Ala Val Val
        275                 280                 285

Gly Ile Val Val Tyr Ala Gly His Glu Thr Lys Ala Met Leu Asn Asn
    290                 295                 300

Ser Gly Pro Arg Tyr Lys Arg Ser Lys Leu Glu Arg Arg Ala Asn Thr
305                 310                 315                 320

Asp Val Leu Trp Cys Val Met Leu Leu Val Ile Met Cys Leu Thr Gly
                325                 330                 335

Ala Val Gly His Gly Ile Trp Leu Ser Arg Tyr Glu Lys Met His Phe
            340                 345                 350

Phe Asn Val Pro Glu Pro Asp Gly His Ile Ile Ser Pro Leu Leu Ala
        355                 360                 365

Gly Phe Tyr Met Phe Trp Thr Met Ile Ile Leu Leu Gln Val Leu Ile
    370                 375                 380

Pro Ile Ser Leu Tyr Val Ser Ile Glu Ile Val Lys Leu Gly Gln Ile
385                 390                 395                 400

Tyr Phe Ile Gln Ser Asp Val Asp Phe Tyr Asn Glu Lys Met Asp Ser
                405                 410                 415

Ile Val Gln Cys Arg Ala Leu Asn Ile Ala Glu Asp Leu Gly Gln Ile
            420                 425                 430

Gln Tyr Leu Phe Ser Asp Lys Thr Gly Thr Leu Thr Glu Asn Lys Met
        435                 440                 445

Val Phe Arg Arg Cys Ser Val Ala Gly Phe Asp Tyr Cys His Glu Glu
    450                 455                 460

Asn Ala Arg Arg Leu Glu Ser Tyr Gln Glu Ala Val Ser Glu Asp Glu
465                 470                 475                 480

Asp Phe Ile Asp Thr Val Ser Gly Ser Leu Ser Asn Met Ala Lys Pro
                485                 490                 495

Arg Ala Pro Ser Cys Arg Thr Val His Asn Gly Pro Leu Gly Asn Lys
            500                 505                 510

Pro Ser Asn His Leu Ala Gly Ser Ser Phe Thr Leu Gly Ser Gly Glu
        515                 520                 525

Gly Ala Ser Glu Val Pro His Ser Arg Gln Ala Ala Phe Ser Ser Pro
    530                 535                 540

Ile Glu Thr Asp Val Val Pro Asp Thr Arg Leu Leu Asp Lys Phe Ser
545                 550                 555                 560

Gln Ile Thr Pro Arg Leu Phe Met Pro Leu Asp Glu Thr Ile Gln Asn
                565                 570                 575

Pro Pro Met Glu Thr Leu Tyr Ile Ile Asp Phe Phe Ile Ala Leu Ala
            580                 585                 590

Ile Cys Asn Thr Val Val Val Ser Ala Pro Asn Gln Pro Arg Gln Lys
        595                 600                 605

Ile Arg His Pro Ser Leu Gly Gly Leu Pro Ile Lys Ser Leu Glu Glu
    610                 615                 620

Ile Lys Ser Leu Phe Gln Arg Trp Ser Val Arg Arg Ser Ser Ser Pro
625                 630                 635                 640
```

-continued

```
Ser Leu Asn Ser Gly Lys Glu Pro Ser Ser Gly Val Pro Asn Ala Phe
                645                 650                 655

Val Ser Arg Leu Pro Leu Phe Ser Arg Met Lys Pro Ala Ser Pro Val
            660                 665                 670

Glu Glu Glu Val Ser Gln Val Cys Glu Ser Pro Gln Cys Ser Ser Ser
        675                 680                 685

Ser Ala Cys Cys Thr Glu Thr Glu Lys Gln His Gly Asp Ala Gly Leu
    690                 695                 700

Leu Asn Gly Lys Ala Glu Ser Leu Pro Gly Gln Pro Leu Ala Cys Asn
705                 710                 715                 720

Leu Cys Tyr Glu Ala Glu Ser Pro Asp Glu Ala Ala Leu Val Tyr Ala
                725                 730                 735

Ala Arg Ala Tyr Gln Cys Thr Leu Arg Ser Arg Thr Pro Glu Gln Val
            740                 745                 750

Met Val Asp Phe Ala Ala Leu Gly Pro Leu Thr Phe Gln Leu Leu His
        755                 760                 765

Ile Leu Pro Phe Asp Ser Val Arg Lys Arg Met Ser Val Val Val Arg
    770                 775                 780

His Pro Leu Ser Asn Gln Val Val Val Tyr Thr Lys Gly Ala Asp Ser
785                 790                 795                 800

Val Ile Met Glu Leu Leu Ser Val Ala Ser Pro Asp Gly Ala Ser Leu
                805                 810                 815

Glu Lys Gln Gln Met Ile Val Arg Glu Lys Thr Gln Lys His Leu Asp
            820                 825                 830

Asp Tyr Ala Lys Gln Gly Leu Arg Thr Leu Cys Ile Ala Lys Lys Val
        835                 840                 845

Met Ser Asp Thr Glu Tyr Ala Glu Trp Leu Arg Asn His Phe Leu Ala
    850                 855                 860

Glu Thr Ser Ile Asp Asn Arg Glu Glu Leu Leu Leu Glu Ser Ala Met
865                 870                 875                 880

Arg Leu Glu Asn Lys Leu Thr Leu Leu Gly Ala Thr Gly Ile Glu Asp
                885                 890                 895

Arg Leu Gln Glu Gly Val Pro Glu Ser Ile Glu Ala Leu His Lys Ala
            900                 905                 910

Gly Ile Lys Ile Trp Met Leu Thr Gly Asp Lys Gln Glu Thr Ala Val
        915                 920                 925

Asn Ile Ala Tyr Ala Cys Lys Leu Leu Glu Pro Asp Asp Lys Leu Phe
    930                 935                 940

Ile Leu Asn Thr Gln Ser Lys Val Arg Ile Leu Arg Leu Asn Leu Phe
945                 950                 955                 960

Phe Cys Ile Phe Lys Gly Ile Gly Thr Phe Glu Ile
                965                 970
```

<210> SEQ ID NO 3
<211> LENGTH: 375
<212> TYPE: DNA
<213> ORGANISM: homo sapiens

<400> SEQUENCE: 3

```
atgagtgaca ctgaatatgc agagtggctg aggaatcatt ttttagctga aaccagcatt     60

gacaacaggg aagaattact acttgaatct gccatgaggt tggagaacaa acttacatta    120

cttggtgcta ctggcattga agaccgtctg caggagggag tccctgaatc tatagaagct    180

cttcacaaag cgggcatcaa gatctggatg ctgacagggg acaagcagga gacagctgtc    240
```

-continued aacatagctt atgcatgcaa actactggag ccagatgaca agctttttat cctcaatacc 300
caaagtaaag tgcgtatatt gagattaaat ctgttcttct gtattttcaa aggcattgga 360
acatttgaga tttga 375

<210> SEQ ID NO 4
<211> LENGTH: 124
<212> TYPE: PRT
<213> ORGANISM: homo sapiens

<400> SEQUENCE: 4

Met Ser Asp Thr Glu Tyr Ala Glu Trp Leu Arg Asn His Phe Leu Ala
1 5 10 15

Glu Thr Ser Ile Asp Asn Arg Glu Glu Leu Leu Leu Glu Ser Ala Met
20 25 30

Arg Leu Glu Asn Lys Leu Thr Leu Leu Gly Ala Thr Gly Ile Glu Asp
35 40 45

Arg Leu Gln Glu Gly Val Pro Glu Ser Ile Glu Ala Leu His Lys Ala
50 55 60

Gly Ile Lys Ile Trp Met Leu Thr Gly Asp Lys Gln Glu Thr Ala Val
65 70 75 80

Asn Ile Ala Tyr Ala Cys Lys Leu Leu Glu Pro Asp Asp Lys Leu Phe
85 90 95

Ile Leu Asn Thr Gln Ser Lys Val Arg Ile Leu Arg Leu Asn Leu Phe
100 105 110

Phe Cys Ile Phe Lys Gly Ile Gly Thr Phe Glu Ile
115 120

<210> SEQ ID NO 5
<211> LENGTH: 3171
<212> TYPE: DNA
<213> ORGANISM: homo sapiens

<400> SEQUENCE: 5
atgactgagg ctctccaatg ggccagatat cactggcgac ggctgatcag aggtgcaacc 60
agggatgatg attcagggcc atacaactat tcctcgttgc tcgcctgtgg gcgcaagtcc 120
tctcagatcc ctaaactgtc aggaaggcac cggattgttg ttccccacat ccagcccttc 180
aaggatgagt atgagaagtt ctccggagcc tatgtgaaca atcgaatacg aacaacaaag 240
tacacacttc tgaattttgt gccaagaaat ttatttgaac aatttcacag agctgccaat 300
ttatatttcc tgttcctagt tgtcctgaac tgggtacctt tggtagaagc cttccaaaag 360
gaaatcacca tgttgcctct ggtggtggtc cttacaatta tcgcaattaa agatggcctg 420
gaagattatc ggaaatacaa aattgacaaa cagatcaata atttaataac taaagtttat 480
agtaggaaag agaaaaaata cattgaccga tgctggaaag acgttactgt tggggacttt 540
attcgcctct cctgcaacga ggtcatccct gcagacatgg tactactctt ttccactgat 600
ccagatggaa tctgtcacat tgagacttct ggtcttgatg gagagagcaa tttaaaacag 660
aggcaggtgg ttcggggata tgcagaacag gactctgaag ttgatcctga gaagttttcc 720
agtaggatag aatgtgaaag cccaaacaat gacctcagca gattccgagg cttcctagaa 780
cattccaaca aagaacgcgt gggtctcagt aaagaaaatt tgttgcttag aggatgcacc 840
attagaaaca cagaggctgt tgtgggcatt gtggtttatg caggccatga aaccaaagca 900
atgctgaaca acagtgggcc acggtataag cgcagcaaat tagaaagaag agcaaacaca 960
gatgtcctct ggtgtgtcat gcttctggtc ataatgtgct taactggcgc agtaggtcat 1020

-continued

```
ggaatctggc tgagcaggta tgaaaagatg cattttttca atgttcccga gcctgatgga   1080
catatcatat caccactgtt ggcaggattt tatatgtttt ggaccatgat cattttgtta   1140
caggtcttga ttcctatttc tctctatgtt tccatcgaaa ttgtgaagct tggacaaata   1200
tatttcattc aaagtgatgt ggatttctac aatgaaaaaa tggattctat tgttcagtgc   1260
cgagccctga acatcgccga ggatctggga cagattcagt acctcttttc cgataagaca   1320
ggaaccctca ctgagaataa gatggttttt cgaagatgta gtgtggcagg atttgattac   1380
tgccatgaag aaaatgccag gaggttggag tcctatcagg aagctgtctc tgaagatgaa   1440
gattttatag acacagtcag tggttccctc agcaatatgg caaaaccgag agcccccagc   1500
tgcaggacag ttcataatgg gcctttggga aataagccct caaatcatct tgctgggagc   1560
tcttttactc taggaagtgg agaaggagcc agtgaagtgc ctcattccag acaggctgct   1620
ttcagtagcc ccattgaaac agacgtggta ccagacacca ggcttttaga caaatttagt   1680
cagattacac ctcggctctt tatgccacta gatgagacca tccaaaatcc accaatggaa   1740
actttgtaca ttatcgactt tttcattgca ttggcaattt gcaacacagt agtggtttct   1800
gctcctaacc aaccccgaca aaagatcaga cacccttcac tggggggggtt gcccattaag   1860
tctttggaag agattaaaag tcttttccag agatggtctg tccgaagatc aagttctcca   1920
tcgcttaaca gtgggaaaga gccatcttct ggagttccaa acgcctttgt gagcagactc   1980
cctctcttta gtcgaatgaa accagcttca cctgtggagg aagaggtctc ccaggtgtgt   2040
gagagccccc agtgctccag tagctcagct tgctgcacag aaacagagaa acaacacggt   2100
gatgcaggcc tcctgaatgg caaggcagag tccctccctg gacagccatt ggcctgcaac   2160
ctgtgttatg aggccgagag cccagacgaa gcggccttag tgtatgccgc cagggcttac   2220
caatgcactt tacggtctcg gacaccagag caggtcatgg tggactttgc tgctttggga   2280
ccattaacat ttcaactcct acacatcctg ccctttgact cagtaagaaa aagaatgtct   2340
gttgtggtcc gacaccctct ttccaatcaa gttgtggtgt atacgaaagg cgctgattct   2400
gtgatcatgg agttactgtc ggtggcttcc ccagatggag caagtctgga gaaacaacag   2460
atgatagtaa gggagaaaac ccagaagcac ttggatgact atgccaaaca aggccttcgt   2520
actttatgta tagcaaagaa ggtcatgagt gacactgaat atgcagagtg gctgaggaat   2580
catttttttag ctgaaaccag cattgacaac agggaagaat tactacttga atctgccatg   2640
aggttggaga acaaacttac attacttggt gctactggca ttgaagaccg tctgcaggag   2700
ggagtccctg aatctataga agctcttcac aaagcgggca tcaagatctg gatgctgaca   2760
ggggacaagc aggagacagc tgtcaacata gcttatgcat gcaaactact ggagccagat   2820
gacaagcttt ttatcctcaa tacccaaagt aaagatgcct gtgggatgct gatgagcaca   2880
attttgaaag aacttcagaa gaaaactcaa gccctgccag agcaagtgtc attaagtgaa   2940
gatttacttc agcctcctgt cccccgggac tcagggttac gagctggact cattatcact   3000
gggaagaccc tggagtttgc cctgcaagaa agtctgcaaa agcagttcct ggaactgaca   3060
tcttggtgtc aagctgtggt ctgctgccga gccacaccgc tgcagaaaag tgaagtggtg   3120
aaattggtcc gcagccatct ccaggtgatg acccttgcta ttggtgagtg a             3171
```

<210> SEQ ID NO 6
<211> LENGTH: 1056
<212> TYPE: PRT
<213> ORGANISM: homo sapiens -continued

<400> SEQUENCE: 6

```
Met Thr Glu Ala Leu Gln Trp Ala Arg Tyr His Trp Arg Arg Leu Ile
 1               5                  10                  15

Arg Gly Ala Thr Arg Asp Asp Asp Ser Gly Pro Tyr Asn Tyr Ser Ser
            20                  25                  30

Leu Leu Ala Cys Gly Arg Lys Ser Ser Gln Ile Pro Lys Leu Ser Gly
        35                  40                  45

Arg His Arg Ile Val Val Pro His Ile Gln Pro Phe Lys Asp Glu Tyr
    50                  55                  60

Glu Lys Phe Ser Gly Ala Tyr Val Asn Asn Arg Ile Arg Thr Thr Lys
65                  70                  75                  80

Tyr Thr Leu Leu Asn Phe Val Pro Arg Asn Leu Phe Glu Gln Phe His
                85                  90                  95

Arg Ala Ala Asn Leu Tyr Phe Leu Phe Leu Val Val Leu Asn Trp Val
            100                 105                 110

Pro Leu Val Glu Ala Phe Gln Lys Glu Ile Thr Met Leu Pro Leu Val
        115                 120                 125

Val Val Leu Thr Ile Ile Ala Ile Lys Asp Gly Leu Glu Asp Tyr Arg
    130                 135                 140

Lys Tyr Lys Ile Asp Lys Gln Ile Asn Asn Leu Ile Thr Lys Val Tyr
145                 150                 155                 160

Ser Arg Lys Glu Lys Lys Tyr Ile Asp Arg Cys Trp Lys Asp Val Thr
                165                 170                 175

Val Gly Asp Phe Ile Arg Leu Ser Cys Asn Glu Val Ile Pro Ala Asp
            180                 185                 190

Met Val Leu Leu Phe Ser Thr Asp Pro Asp Gly Ile Cys His Ile Glu
        195                 200                 205

Thr Ser Gly Leu Asp Gly Glu Ser Asn Leu Lys Gln Arg Gln Val Val
    210                 215                 220

Arg Gly Tyr Ala Glu Gln Asp Ser Glu Val Asp Pro Glu Lys Phe Ser
225                 230                 235                 240

Ser Arg Ile Glu Cys Glu Ser Pro Asn Asn Asp Leu Ser Arg Phe Arg
                245                 250                 255

Gly Phe Leu Glu His Ser Asn Lys Glu Arg Val Gly Leu Ser Lys Glu
            260                 265                 270

Asn Leu Leu Leu Arg Gly Cys Thr Ile Arg Asn Thr Glu Ala Val Val
        275                 280                 285

Gly Ile Val Val Tyr Ala Gly His Glu Thr Lys Ala Met Leu Asn Asn
    290                 295                 300

Ser Gly Pro Arg Tyr Lys Arg Ser Lys Leu Glu Arg Arg Ala Asn Thr
305                 310                 315                 320

Asp Val Leu Trp Cys Val Met Leu Leu Val Ile Met Cys Leu Thr Gly
                325                 330                 335

Ala Val Gly His Gly Ile Trp Leu Ser Arg Tyr Glu Lys Met His Phe
            340                 345                 350

Phe Asn Val Pro Glu Pro Asp Gly His Ile Ile Ser Pro Leu Leu Ala
        355                 360                 365

Gly Phe Tyr Met Phe Trp Thr Met Ile Ile Leu Leu Gln Val Leu Ile
    370                 375                 380

Pro Ile Ser Leu Tyr Val Ser Ile Glu Ile Val Lys Leu Gly Gln Ile
385                 390                 395                 400

Tyr Phe Ile Gln Ser Asp Val Asp Phe Tyr Asn Glu Lys Met Asp Ser
                405                 410                 415
```

-continued

```
Ile Val Gln Cys Arg Ala Leu Asn Ile Ala Glu Asp Leu Gly Gln Ile
            420                 425                 430

Gln Tyr Leu Phe Ser Asp Lys Thr Gly Thr Leu Thr Glu Asn Lys Met
        435                 440                 445

Val Phe Arg Arg Cys Ser Val Ala Gly Phe Asp Tyr Cys His Glu Glu
    450                 455                 460

Asn Ala Arg Arg Leu Glu Ser Tyr Gln Glu Ala Val Ser Glu Asp Glu
465                 470                 475                 480

Asp Phe Ile Asp Thr Val Ser Gly Ser Leu Ser Asn Met Ala Lys Pro
                485                 490                 495

Arg Ala Pro Ser Cys Arg Thr Val His Asn Gly Pro Leu Gly Asn Lys
            500                 505                 510

Pro Ser Asn His Leu Ala Gly Ser Ser Phe Thr Leu Gly Ser Gly Glu
        515                 520                 525

Gly Ala Ser Glu Val Pro His Ser Arg Gln Ala Ala Phe Ser Ser Pro
    530                 535                 540

Ile Glu Thr Asp Val Val Pro Asp Thr Arg Leu Leu Asp Lys Phe Ser
545                 550                 555                 560

Gln Ile Thr Pro Arg Leu Phe Met Pro Leu Asp Glu Thr Ile Gln Asn
                565                 570                 575

Pro Pro Met Glu Thr Leu Tyr Ile Ile Asp Phe Phe Ile Ala Leu Ala
            580                 585                 590

Ile Cys Asn Thr Val Val Val Ser Ala Pro Asn Gln Pro Arg Gln Lys
        595                 600                 605

Ile Arg His Pro Ser Leu Gly Gly Leu Pro Ile Lys Ser Leu Glu Glu
    610                 615                 620

Ile Lys Ser Leu Phe Gln Arg Trp Ser Val Arg Arg Ser Ser Ser Pro
625                 630                 635                 640

Ser Leu Asn Ser Gly Lys Glu Pro Ser Ser Gly Val Pro Asn Ala Phe
                645                 650                 655

Val Ser Arg Leu Pro Leu Phe Ser Arg Met Lys Pro Ala Ser Pro Val
            660                 665                 670

Glu Glu Glu Val Ser Gln Val Cys Glu Ser Pro Gln Cys Ser Ser Ser
        675                 680                 685

Ser Ala Cys Cys Thr Glu Thr Glu Lys Gln His Gly Asp Ala Gly Leu
    690                 695                 700

Leu Asn Gly Lys Ala Glu Ser Leu Pro Gly Gln Pro Leu Ala Cys Asn
705                 710                 715                 720

Leu Cys Tyr Glu Ala Glu Ser Pro Asp Glu Ala Ala Leu Val Tyr Ala
                725                 730                 735

Ala Arg Ala Tyr Gln Cys Thr Leu Arg Ser Arg Thr Pro Glu Gln Val
            740                 745                 750

Met Val Asp Phe Ala Ala Leu Gly Pro Leu Thr Phe Gln Leu Leu His
        755                 760                 765

Ile Leu Pro Phe Asp Ser Val Arg Lys Arg Met Ser Val Val Val Arg
    770                 775                 780

His Pro Leu Ser Asn Gln Val Val Val Tyr Thr Lys Gly Ala Asp Ser
785                 790                 795                 800

Val Ile Met Glu Leu Leu Ser Val Ala Ser Pro Asp Gly Ala Ser Leu
                805                 810                 815

Glu Lys Gln Gln Met Ile Val Arg Glu Lys Thr Gln Lys His Leu Asp
            820                 825                 830
```

-continued

```
Asp Tyr Ala Lys Gln Gly Leu Arg Thr Leu Cys Ile Ala Lys Lys Val
        835                 840                 845

Met Ser Asp Thr Glu Tyr Ala Glu Trp Leu Arg Asn His Phe Leu Ala
    850                 855                 860

Glu Thr Ser Ile Asp Asn Arg Glu Glu Leu Leu Leu Glu Ser Ala Met
865                 870                 875                 880

Arg Leu Glu Asn Lys Leu Thr Leu Leu Gly Ala Thr Gly Ile Glu Asp
                885                 890                 895

Arg Leu Gln Glu Gly Val Pro Glu Ser Ile Glu Ala Leu His Lys Ala
            900                 905                 910

Gly Ile Lys Ile Trp Met Leu Thr Gly Asp Lys Gln Glu Thr Ala Val
        915                 920                 925

Asn Ile Ala Tyr Ala Cys Lys Leu Leu Glu Pro Asp Asp Lys Leu Phe
    930                 935                 940

Ile Leu Asn Thr Gln Ser Lys Asp Ala Cys Gly Met Leu Met Ser Thr
945                 950                 955                 960

Ile Leu Lys Glu Leu Gln Lys Lys Thr Gln Ala Leu Pro Glu Gln Val
                965                 970                 975

Ser Leu Ser Glu Asp Leu Leu Gln Pro Pro Val Pro Arg Asp Ser Gly
            980                 985                 990

Leu Arg Ala Gly Leu Ile Ile Thr Gly Lys Thr Leu Glu Phe Ala Leu
        995                 1000                1005

Gln Glu Ser Leu Gln Lys Gln Phe Leu Glu Leu Thr Ser Trp Cys Gln
    1010                1015                1020

Ala Val Val Cys Cys Arg Ala Thr Pro Leu Gln Lys Ser Glu Val Val
1025                1030                1035                1040

Lys Leu Val Arg Ser His Leu Gln Val Met Thr Leu Ala Ile Gly Glu
                1045                1050                1055
```

<210> SEQ ID NO 7
<211> LENGTH: 627
<212> TYPE: DNA
<213> ORGANISM: homo sapiens

<400> SEQUENCE: 7

```
atgagtgaca ctgaatatgc agagtggctg aggaatcatt ttttagctga aaccagcatt      60

gacaacaggg aagaattact acttgaatct gccatgaggt tggagaacaa acttacatta     120

cttggtgcta ctggcattga agaccgtctg caggagggag tccctgaatc tatagaagct     180

cttcacaaag cgggcatcaa gatctggatg ctgacagggg acaagcagga gacagctgtc     240

aacatagctt atgcatgcaa actactggag ccagatgaca agctttttat cctcaatacc     300

caaagtaaag atgcctgtgg gatgctgatg agcacaattt tgaaagaact tcagaagaaa     360

actcaagccc tgccagagca agtgtcatta agtgaagatt tacttcagcc tcctgtcccc     420

cgggactcag ggttacgagc tggactcatt atcactggga agaccctgga gtttgccctg     480

caagaaagtc tgcaaaagca gttcctggaa ctgacatctt ggtgtcaagc tgtggtctgc     540

tgccgagcca caccgctgca gaaaagtgaa gtggtgaaat tggtccgcag ccatctccag     600

gtgatgaccc ttgctattgg tgagtga                                         627
```

<210> SEQ ID NO 8
<211> LENGTH: 208
<212> TYPE: PRT
<213> ORGANISM: homo sapiens -continued

<400> SEQUENCE: 8

```
Met Ser Asp Thr Glu Tyr Ala Glu Trp Leu Arg Asn His Phe Leu Ala
 1               5                  10                  15

Glu Thr Ser Ile Asp Asn Arg Glu Glu Leu Leu Leu Glu Ser Ala Met
            20                  25                  30

Arg Leu Glu Asn Lys Leu Thr Leu Leu Gly Ala Thr Gly Ile Glu Asp
        35                  40                  45

Arg Leu Gln Glu Gly Val Pro Glu Ser Ile Glu Ala Leu His Lys Ala
    50                  55                  60

Gly Ile Lys Ile Trp Met Leu Thr Gly Asp Lys Gln Glu Thr Ala Val
65                  70                  75                  80

Asn Ile Ala Tyr Ala Cys Lys Leu Leu Glu Pro Asp Asp Lys Leu Phe
                85                  90                  95

Ile Leu Asn Thr Gln Ser Lys Asp Ala Cys Gly Met Leu Met Ser Thr
            100                 105                 110

Ile Leu Lys Glu Leu Gln Lys Lys Thr Gln Ala Leu Pro Glu Gln Val
        115                 120                 125

Ser Leu Ser Glu Asp Leu Leu Gln Pro Pro Val Pro Arg Asp Ser Gly
    130                 135                 140

Leu Arg Ala Gly Leu Ile Ile Thr Gly Lys Thr Leu Glu Phe Ala Leu
145                 150                 155                 160

Gln Glu Ser Leu Gln Lys Gln Phe Leu Glu Leu Thr Ser Trp Cys Gln
                165                 170                 175

Ala Val Val Cys Cys Arg Ala Thr Pro Leu Gln Lys Ser Glu Val Val
            180                 185                 190

Lys Leu Val Arg Ser His Leu Gln Val Met Thr Leu Ala Ile Gly Glu
        195                 200                 205
```

<210> SEQ ID NO 9
<211> LENGTH: 3813
<212> TYPE: DNA
<213> ORGANISM: homo sapiens

<400> SEQUENCE: 9

```
atgactgagg ctctccaatg ggccagatat cactggcgac ggctgatcag aggtgcaacc      60

agggatgatg attcagggcc atacaactat tcctcgttgc tcgcctgtgg gcgcaagtcc     120

tctcagatcc ctaaactgtc aggaaggcac cggattgttg ttccccacat ccagcccttc     180

aaggatgagt atgagaagtt ctccggagcc tatgtgaaca atcgaatacg aacaacaaag     240

tacacacttc tgaattttgt gccaagaaat ttatttgaac aatttcacag agctgccaat     300

ttatatttcc tgttcctagt tgtcctgaac tgggtacctt tggtagaagc cttccaaaag     360

gaaatcacca tgttgcctct ggtggtggtc cttacaatta tcgcaattaa agatggcctg     420

gaagattatc ggaaatacaa aattgacaaa cagatcaata atttaataac taaagtttat     480

agtaggaaag agaaaaaata cattgaccga tgctggaaag acgttactgt tggggacttt     540

attcgcctct cctgcaacga ggtcatccct gcagacatgg tactactctt ttccactgat     600

ccagatggaa tctgtcacat tgagacttct ggtcttgatg gagagagcaa tttaaaacag     660

aggcaggtgg ttcggggata tgcagaacag gactctgaag ttgatcctga gaagttttcc     720

agtaggatag aatgtgaaag cccaaacaat gacctcagca gattccgagg cttcctagaa     780

cattccaaca aagaacgcgt gggtctcagt aaagaaaatt tgttgcttag aggatgcacc     840

attagaaaca cagaggctgt tgtgggcatt gtggtttatg caggccatga aaccaaagca     900
```

-continued

```
atgctgaaca acagtgggcc acggtataag cgcagcaaat tagaaagaag agcaaacaca      960
gatgtcctct ggtgtgtcat gcttctggtc ataatgtgct taactggcgc agtaggtcat     1020
ggaatctggc tgagcaggta tgaaaagatg cattttttca atgttcccga gcctgatgga     1080
catatcatat caccactgtt ggcaggattt tatatgtttt ggaccatgat cattttgtta     1140
caggtcttga ttcctatttc tctctatgtt tccatcgaaa ttgtgaagct tggacaaata     1200
tatttcattc aaagtgatgt ggatttctac aatgaaaaaa tggattctat tgttcagtgc     1260
cgagccctga acatcgccga ggatctggga cagattcagt acctcttttc cgataagaca     1320
ggaaccctca ctgagaataa gatggttttt cgaagatgta gtgtggcagg atttgattac     1380
tgccatgaag aaaatgccag gaggttggag tcctatcagg aagctgtctc tgaagatgaa     1440
gattttatag acacagtcag tggttccctc agcaatatgg caaaaccgag agcccccagc     1500
tgcaggacag ttcataatgg gcctttggga aataagccct caaatcatct tgctgggagc     1560
tcttttactc taggaagtgg agaaggagcc agtgaagtgc ctcattccag acaggctgct     1620
ttcagtagcc ccattgaaac agacgtggta ccagacacca ggcttttaga caaatttagt     1680
cagattacac ctcggctctt tatgccacta gatgagacca tccaaaatcc accaatggaa     1740
actttgtaca ttatcgactt tttcattgca ttggcaattt gcaacacagt agtggtttct     1800
gctcctaacc aaccccgaca aaagatcaga cacccttcac tgggggggtt gcccattaag     1860
tctttggaag agattaaaag tcttttccag agatggtctg tccgaagatc aagttctcca     1920
tcgcttaaca gtgggaaaga gccatcttct ggagttccaa acgcctttgt gagcagactc     1980
cctctcttta gtcgaatgaa accagcttca cctgtggagg aagaggtctc ccaggtgtgt     2040
gagagccccc agtgctccag tagctcagct tgctgcacag aaacagagaa acaacacggt     2100
gatgcaggcc tcctgaatgg caaggcagag tccctccctg gacagccatt ggcctgcaac     2160
ctgtgttatg aggccgagag cccagacgaa gcggccttag tgtatgccgc cagggcttac     2220
caatgcactt tacggtctcg gacaccagag caggtcatgg tggactttgc tgctttggga     2280
ccattaacat ttcaactcct acacatcctg ccctttgact cagtaagaaa aagaatgtct     2340
gttgtggtcc gacaccctct ttccaatcaa gttgtggtgt atacgaaagg cgctgattct     2400
gtgatcatgg agttactgtc ggtggcttcc ccagatggag caagtctgga gaaacaacag     2460
atgatagtaa gggagaaaac ccagaagcac ttggatgact atgccaaaca aggccttcgt     2520
actttatgta tagcaaagaa ggtcatgagt gacactgaat atgcagagtg gctgaggaat     2580
cattttttag ctgaaaccag cattgacaac agggaagaat tactacttga atctgccatg     2640
aggttggaga acaaacttac attacttggt gctactggca ttgaagaccg tctgcaggag     2700
ggagtccctg aatctataga agctcttcac aaagcgggca tcaagatctg gatgctgaca     2760
ggggacaagc aggagacagc tgtcaacata gcttatgcat gcaaactact ggagccagat     2820
gacaagcttt ttatcctcaa tacccaaagt aaagatgcct gtgggatgct gatgagcaca     2880
attttgaaag aacttcagaa gaaaactcaa gccctgccag agcaagtgtc attaagtgaa     2940
gatttacttc agcctcctgt cccccgggac tcagggttac gagctggact cattatcact     3000
gggaagaccc tggagtttgc cctgcaagaa agtctgcaaa agcagttcct ggaactgaca     3060
tcttggtgtc aagctgtggt ctgctgccga gccacaccgc tgcagaaaag tgaagtggtg     3120
aaattggtcc gcagccatct ccaggtgatg acccttgcta ttggtgatgg tgccaatgat     3180
gttagcatga tacaagtggc agacattggg ataggggtct caggtcaaga aggcatgcag     3240
gctgtgatgg ccagtgactt tgccgtttct cagttcaaac atctcagcaa gctccttctt     3300
```

-continued

```
gtccatggac actggtgtta tacacggctt tccaacatga ttctctattt tttctataag   3360

aatgtggcct atgtgaacct ccttttctgg taccagttct tttgtggatt ttcaggaaca   3420

tccatgactg attactgggt tttgatcttc ttcaacctcc tcttcacatc tgcccctcct   3480

gtcatttatg gtgttttgga gaaagatgtg tctgcagaga ccctcatgca actgcctgaa   3540

ctttacagaa gtggtcagaa atcagaggca tacttacccc ataccttctg gatcacctta   3600

ttggatgctt tttatcaaag cctggtctgc ttctttgtgc cttattttac ctaccagggc   3660

tcagatactg acatctttgc atttggaaac cccctgaaca cagccactct gttcatcgtt   3720

ctcctccatc tggtcattga aagcaagagt ttgaccaggt gcagtgactc acacctgcaa   3780

ttccagagct ttgggaggct gtggatcaca tga                                3813
```

<210> SEQ ID NO 10
<211> LENGTH: 1270
<212> TYPE: PRT
<213> ORGANISM: homo sapiens

<400> SEQUENCE: 10

```
Met Thr Glu Ala Leu Gln Trp Ala Arg Tyr His Trp Arg Arg Leu Ile
 1               5                  10                  15

Arg Gly Ala Thr Arg Asp Asp Asp Ser Gly Pro Tyr Asn Tyr Ser Ser
            20                  25                  30

Leu Leu Ala Cys Gly Arg Lys Ser Ser Gln Ile Pro Lys Leu Ser Gly
        35                  40                  45

Arg His Arg Ile Val Val Pro His Ile Gln Pro Phe Lys Asp Glu Tyr
    50                  55                  60

Glu Lys Phe Ser Gly Ala Tyr Val Asn Asn Arg Ile Arg Thr Thr Lys
65                  70                  75                  80

Tyr Thr Leu Leu Asn Phe Val Pro Arg Asn Leu Phe Glu Gln Phe His
                85                  90                  95

Arg Ala Ala Asn Leu Tyr Phe Leu Phe Leu Val Val Leu Asn Trp Val
            100                 105                 110

Pro Leu Val Glu Ala Phe Gln Lys Glu Ile Thr Met Leu Pro Leu Val
        115                 120                 125

Val Val Leu Thr Ile Ile Ala Ile Lys Asp Gly Leu Glu Asp Tyr Arg
    130                 135                 140

Lys Tyr Lys Ile Asp Lys Gln Ile Asn Asn Leu Ile Thr Lys Val Tyr
145                 150                 155                 160

Ser Arg Lys Glu Lys Lys Tyr Ile Asp Arg Cys Trp Lys Asp Val Thr
                165                 170                 175

Val Gly Asp Phe Ile Arg Leu Ser Cys Asn Glu Val Ile Pro Ala Asp
            180                 185                 190

Met Val Leu Leu Phe Ser Thr Asp Pro Asp Gly Ile Cys His Ile Glu
        195                 200                 205

Thr Ser Gly Leu Asp Gly Glu Ser Asn Leu Lys Gln Arg Gln Val Val
    210                 215                 220

Arg Gly Tyr Ala Glu Gln Asp Ser Glu Val Asp Pro Glu Lys Phe Ser
225                 230                 235                 240

Ser Arg Ile Glu Cys Glu Ser Pro Asn Asn Asp Leu Ser Arg Phe Arg
                245                 250                 255

Gly Phe Leu Glu His Ser Asn Lys Glu Arg Val Gly Leu Ser Lys Glu
            260                 265                 270

Asn Leu Leu Leu Arg Gly Cys Thr Ile Arg Asn Thr Glu Ala Val Val
        275                 280                 285
```

-continued

```
Gly Ile Val Val Tyr Ala Gly His Glu Thr Lys Ala Met Leu Asn Asn
    290                 295                 300

Ser Gly Pro Arg Tyr Lys Arg Ser Lys Leu Glu Arg Arg Ala Asn Thr
305                 310                 315                 320

Asp Val Leu Trp Cys Val Met Leu Leu Val Ile Met Cys Leu Thr Gly
                325                 330                 335

Ala Val Gly His Gly Ile Trp Leu Ser Arg Tyr Glu Lys Met His Phe
            340                 345                 350

Phe Asn Val Pro Glu Pro Asp Gly His Ile Ile Ser Pro Leu Leu Ala
        355                 360                 365

Gly Phe Tyr Met Phe Trp Thr Met Ile Ile Leu Leu Gln Val Leu Ile
    370                 375                 380

Pro Ile Ser Leu Tyr Val Ser Ile Glu Ile Val Lys Leu Gly Gln Ile
385                 390                 395                 400

Tyr Phe Ile Gln Ser Asp Val Asp Phe Tyr Asn Glu Lys Met Asp Ser
                405                 410                 415

Ile Val Gln Cys Arg Ala Leu Asn Ile Ala Glu Asp Leu Gly Gln Ile
            420                 425                 430

Gln Tyr Leu Phe Ser Asp Lys Thr Gly Thr Leu Thr Glu Asn Lys Met
        435                 440                 445

Val Phe Arg Arg Cys Ser Val Ala Gly Phe Asp Tyr Cys His Glu Glu
    450                 455                 460

Asn Ala Arg Arg Leu Glu Ser Tyr Gln Glu Ala Val Ser Glu Asp Glu
465                 470                 475                 480

Asp Phe Ile Asp Thr Val Ser Gly Ser Leu Ser Asn Met Ala Lys Pro
                485                 490                 495

Arg Ala Pro Ser Cys Arg Thr Val His Asn Gly Pro Leu Gly Asn Lys
            500                 505                 510

Pro Ser Asn His Leu Ala Gly Ser Ser Phe Thr Leu Gly Ser Gly Glu
        515                 520                 525

Gly Ala Ser Glu Val Pro His Ser Arg Gln Ala Ala Phe Ser Ser Pro
    530                 535                 540

Ile Glu Thr Asp Val Val Pro Asp Thr Arg Leu Leu Asp Lys Phe Ser
545                 550                 555                 560

Gln Ile Thr Pro Arg Leu Phe Met Pro Leu Asp Glu Thr Ile Gln Asn
                565                 570                 575

Pro Pro Met Glu Thr Leu Tyr Ile Ile Asp Phe Phe Ile Ala Leu Ala
            580                 585                 590

Ile Cys Asn Thr Val Val Val Ser Ala Pro Asn Gln Pro Arg Gln Lys
        595                 600                 605

Ile Arg His Pro Ser Leu Gly Gly Leu Pro Ile Lys Ser Leu Glu Glu
    610                 615                 620

Ile Lys Ser Leu Phe Gln Arg Trp Ser Val Arg Arg Ser Ser Ser Pro
625                 630                 635                 640

Ser Leu Asn Ser Gly Lys Glu Pro Ser Ser Gly Val Pro Asn Ala Phe
                645                 650                 655

Val Ser Arg Leu Pro Leu Phe Ser Arg Met Lys Pro Ala Ser Pro Val
            660                 665                 670

Glu Glu Glu Val Ser Gln Val Cys Glu Ser Pro Gln Cys Ser Ser Ser
        675                 680                 685

Ser Ala Cys Cys Thr Glu Thr Glu Lys Gln His Gly Asp Ala Gly Leu
    690                 695                 700
```

-continued

```
Leu Asn Gly Lys Ala Glu Ser Leu Pro Gly Gln Pro Leu Ala Cys Asn
705                 710                 715                 720

Leu Cys Tyr Glu Ala Glu Ser Pro Asp Glu Ala Ala Leu Val Tyr Ala
                725                 730                 735

Ala Arg Ala Tyr Gln Cys Thr Leu Arg Ser Arg Thr Pro Glu Gln Val
            740                 745                 750

Met Val Asp Phe Ala Ala Leu Gly Pro Leu Thr Phe Gln Leu Leu His
        755                 760                 765

Ile Leu Pro Phe Asp Ser Val Arg Lys Arg Met Ser Val Val Val Arg
    770                 775                 780

His Pro Leu Ser Asn Gln Val Val Val Tyr Thr Lys Gly Ala Asp Ser
785                 790                 795                 800

Val Ile Met Glu Leu Leu Ser Val Ala Ser Pro Asp Gly Ala Ser Leu
                805                 810                 815

Glu Lys Gln Gln Met Ile Val Arg Glu Lys Thr Gln Lys His Leu Asp
            820                 825                 830

Asp Tyr Ala Lys Gln Gly Leu Arg Thr Leu Cys Ile Ala Lys Lys Val
        835                 840                 845

Met Ser Asp Thr Glu Tyr Ala Glu Trp Leu Arg Asn His Phe Leu Ala
    850                 855                 860

Glu Thr Ser Ile Asp Asn Arg Glu Glu Leu Leu Leu Glu Ser Ala Met
865                 870                 875                 880

Arg Leu Glu Asn Lys Leu Thr Leu Leu Gly Ala Thr Gly Ile Glu Asp
                885                 890                 895

Arg Leu Gln Glu Gly Val Pro Glu Ser Ile Glu Ala Leu His Lys Ala
            900                 905                 910

Gly Ile Lys Ile Trp Met Leu Thr Gly Asp Lys Gln Glu Thr Ala Val
        915                 920                 925

Asn Ile Ala Tyr Ala Cys Lys Leu Leu Glu Pro Asp Asp Lys Leu Phe
    930                 935                 940

Ile Leu Asn Thr Gln Ser Lys Asp Ala Cys Gly Met Leu Met Ser Thr
945                 950                 955                 960

Ile Leu Lys Glu Leu Gln Lys Lys Thr Gln Ala Leu Pro Glu Gln Val
                965                 970                 975

Ser Leu Ser Glu Asp Leu Leu Gln Pro Pro Val Pro Arg Asp Ser Gly
            980                 985                 990

Leu Arg Ala Gly Leu Ile Ile Thr Gly Lys Thr Leu Glu Phe Ala Leu
        995                 1000                1005

Gln Glu Ser Leu Gln Lys Gln Phe Leu Glu Leu Thr Ser Trp Cys Gln
    1010                1015                1020

Ala Val Val Cys Cys Arg Ala Thr Pro Leu Gln Lys Ser Glu Val Val
1025                1030                1035                1040

Lys Leu Val Arg Ser His Leu Gln Val Met Thr Leu Ala Ile Gly Asp
                1045                1050                1055

Gly Ala Asn Asp Val Ser Met Ile Gln Val Ala Asp Ile Gly Ile Gly
            1060                1065                1070

Val Ser Gly Gln Glu Gly Met Gln Ala Val Met Ala Ser Asp Phe Ala
        1075                1080                1085

Val Ser Gln Phe Lys His Leu Ser Lys Leu Leu Leu Val His Gly His
    1090                1095                1100

Trp Cys Tyr Thr Arg Leu Ser Asn Met Ile Leu Tyr Phe Phe Tyr Lys
1105                1110                1115                1120
```

-continued

```
Asn Val Ala Tyr Val Asn Leu Leu Phe Trp Tyr Gln Phe Phe Cys Gly
                1125                1130                1135

Phe Ser Gly Thr Ser Met Thr Asp Tyr Trp Val Leu Ile Phe Phe Asn
            1140                1145                1150

Leu Leu Phe Thr Ser Ala Pro Pro Val Ile Tyr Gly Val Leu Glu Lys
        1155                1160                1165

Asp Val Ser Ala Glu Thr Leu Met Gln Leu Pro Glu Leu Tyr Arg Ser
    1170                1175                1180

Gly Gln Lys Ser Glu Ala Tyr Leu Pro His Thr Phe Trp Ile Thr Leu
1185                1190                1195                1200

Leu Asp Ala Phe Tyr Gln Ser Leu Val Cys Phe Phe Val Pro Tyr Phe
                1205                1210                1215

Thr Tyr Gln Gly Ser Asp Thr Asp Ile Phe Ala Phe Gly Asn Pro Leu
            1220                1225                1230

Asn Thr Ala Thr Leu Phe Ile Val Leu Leu His Leu Val Ile Glu Ser
        1235                1240                1245

Lys Ser Leu Thr Arg Cys Ser Asp Ser His Leu Gln Phe Gln Ser Phe
    1250                1255                1260

Gly Arg Leu Trp Ile Thr
1265                1270


<210> SEQ ID NO 11
<211> LENGTH: 1269
<212> TYPE: DNA
<213> ORGANISM: homo sapiens

<400> SEQUENCE: 11

atgagtgaca ctgaatatgc agagtggctg aggaatcatt ttttagctga aaccagcatt     60

gacaacaggg aagaattact acttgaatct gccatgaggt tggagaacaa acttacatta    120

cttggtgcta ctggcattga agaccgtctg caggagggag tccctgaatc tatagaagct    180

cttcacaaag cgggcatcaa gatctggatg ctgacagggg acaagcagga gacagctgtc    240

aacatagctt atgcatgcaa actactggag ccagatgaca agctttttat cctcaatacc    300

caaagtaaag atgcctgtgg gatgctgatg agcacaattt tgaaagaact tcagaagaaa    360

actcaagccc tgccagagca agtgtcatta agtgaagatt tacttcagcc tcctgtcccc    420

cgggactcag ggttacgagc tggactcatt atcactggga agaccctgga gtttgccctg    480

caagaaagtc tgcaaaagca gttcctggaa ctgacatctt ggtgtcaagc tgtggtctgc    540

tgccgagcca caccgctgca gaaaagtgaa gtggtgaaat tggtccgcag ccatctccag    600

gtgatgaccc ttgctattgg tgatggtgcc aatgatgtta gcatgataca agtggcagac    660

attgggatag ggtctcagg tcaagaaggc atgcaggctg tgatggccag tgactttgcc     720

gtttctcagt tcaaacatct cagcaagctc cttcttgtcc atggacactg gtgttataca    780

cggctttcca acatgattct ctattttttc tataagaatg tggcctatgt gaacctcctt    840

ttctggtacc agttcttttg tggattttca ggaacatcca tgactgatta ctgggttttg    900

atcttcttca acctcctctt cacatctgcc cctcctgtca tttatggtgt tttggagaaa    960

gatgtgtctg cagagaccct catgcaactg cctgaacttt acagaagtgg tcagaaatca   1020

gaggcatact taccccatac cttctggatc accttattgg atgcttttta tcaaagcctg   1080

gtctgcttct ttgtgcctta ttttacctac cagggctcag atactgacat ctttgcattt   1140

ggaaaccccc tgaacacagc cactctgttc atcgttctcc tccatctggt cattgaaagc   1200
```

-continued

```
aagagtttga ccaggtgcag tgactcacac ctgcaattcc agagctttgg gaggctgtgg   1260

atcacatga                                                           1269


<210> SEQ ID NO 12
<211> LENGTH: 422
<212> TYPE: PRT
<213> ORGANISM: homo sapiens

<400> SEQUENCE: 12

Met Ser Asp Thr Glu Tyr Ala Glu Trp Leu Arg Asn His Phe Leu Ala
 1               5                  10                  15

Glu Thr Ser Ile Asp Asn Arg Glu Glu Leu Leu Leu Glu Ser Ala Met
            20                  25                  30

Arg Leu Glu Asn Lys Leu Thr Leu Leu Gly Ala Thr Gly Ile Glu Asp
        35                  40                  45

Arg Leu Gln Glu Gly Val Pro Glu Ser Ile Glu Ala Leu His Lys Ala
    50                  55                  60

Gly Ile Lys Ile Trp Met Leu Thr Gly Asp Lys Gln Glu Thr Ala Val
65                  70                  75                  80

Asn Ile Ala Tyr Ala Cys Lys Leu Leu Glu Pro Asp Asp Lys Leu Phe
                85                  90                  95

Ile Leu Asn Thr Gln Ser Lys Asp Ala Cys Gly Met Leu Met Ser Thr
            100                 105                 110

Ile Leu Lys Glu Leu Gln Lys Lys Thr Gln Ala Leu Pro Glu Gln Val
        115                 120                 125

Ser Leu Ser Glu Asp Leu Leu Gln Pro Pro Val Pro Arg Asp Ser Gly
    130                 135                 140

Leu Arg Ala Gly Leu Ile Ile Thr Gly Lys Thr Leu Glu Phe Ala Leu
145                 150                 155                 160

Gln Glu Ser Leu Gln Lys Gln Phe Leu Glu Leu Thr Ser Trp Cys Gln
                165                 170                 175

Ala Val Val Cys Cys Arg Ala Thr Pro Leu Gln Lys Ser Glu Val Val
            180                 185                 190

Lys Leu Val Arg Ser His Leu Gln Val Met Thr Leu Ala Ile Gly Asp
        195                 200                 205

Gly Ala Asn Asp Val Ser Met Ile Gln Val Ala Asp Ile Gly Ile Gly
    210                 215                 220

Val Ser Gly Gln Glu Gly Met Gln Ala Val Met Ala Ser Asp Phe Ala
225                 230                 235                 240

Val Ser Gln Phe Lys His Leu Ser Lys Leu Leu Leu Val His Gly His
                245                 250                 255

Trp Cys Tyr Thr Arg Leu Ser Asn Met Ile Leu Tyr Phe Phe Tyr Lys
            260                 265                 270

Asn Val Ala Tyr Val Asn Leu Leu Phe Trp Tyr Gln Phe Phe Cys Gly
        275                 280                 285

Phe Ser Gly Thr Ser Met Thr Asp Tyr Trp Val Leu Ile Phe Phe Asn
    290                 295                 300

Leu Leu Phe Thr Ser Ala Pro Pro Val Ile Tyr Gly Val Leu Glu Lys
305                 310                 315                 320

Asp Val Ser Ala Glu Thr Leu Met Gln Leu Pro Glu Leu Tyr Arg Ser
                325                 330                 335

Gly Gln Lys Ser Glu Ala Tyr Leu Pro His Thr Phe Trp Ile Thr Leu
            340                 345                 350
```

-continued

```
Leu Asp Ala Phe Tyr Gln Ser Leu Val Cys Phe Phe Val Pro Tyr Phe
        355                 360                 365

Thr Tyr Gln Gly Ser Asp Thr Asp Ile Phe Ala Phe Gly Asn Pro Leu
    370                 375                 380

Asn Thr Ala Thr Leu Phe Ile Val Leu Leu His Leu Val Ile Glu Ser
385                 390                 395                 400

Lys Ser Leu Thr Arg Cys Ser Asp Ser His Leu Gln Phe Gln Ser Phe
                405                 410                 415

Gly Arg Leu Trp Ile Thr
            420


<210> SEQ ID NO 13
<211> LENGTH: 4281
<212> TYPE: DNA
<213> ORGANISM: homo sapiens

<400> SEQUENCE: 13

atgactgagg ctctccaatg ggccagatat cactggcgac ggctgatcag aggtgcaacc     60

agggatgatg attcagggcc atacaactat tcctcgttgc tcgcctgtgg gcgcaagtcc    120

tctcagatcc ctaaactgtc aggaaggcac cggattgttg ttccccacat ccagcccttc    180

aaggatgagt atgagaagtt ctccggagcc tatgtgaaca atcgaatacg aacaacaaag    240

tacacacttc tgaattttgt gccaagaaat ttatttgaac aatttcacag agctgccaat    300

ttatatttcc tgttcctagt tgtcctgaac tgggtacctt tggtagaagc cttccaaaag    360

gaaatcacca tgttgcctct ggtggtggtc cttacaatta tcgcaattaa agatggcctg    420

gaagattatc ggaaatacaa aattgacaaa cagatcaata atttaataac taaagtttat    480

agtaggaaag agaaaaaata cattgaccga tgctggaaag acgttactgt tggggacttt    540

attcgcctct cctgcaacga ggtcatccct gcagacatgg tactactctt ttccactgat    600

ccagatggaa tctgtcacat tgagacttct ggtcttgatg gagagagcaa tttaaaacag    660

aggcaggtgg ttcggggata tgcagaacag gactctgaag ttgatcctga gaagttttcc    720

agtaggatag aatgtgaaag cccaaacaat gacctcagca gattccgagg cttcctagaa    780

cattccaaca aagaacgcgt gggtctcagt aaagaaaatt tgttgcttag aggatgcacc    840

attagaaaca cagaggctgt tgtgggcatt gtggtttatg caggccatga aaccaaagca    900

atgctgaaca acagtgggcc acggtataag cgcagcaaat tagaaagaag agcaaacaca    960

gatgtcctct ggtgtgtcat gcttctggtc ataatgtgct taactggcgc agtaggtcat   1020

ggaatctggc tgagcaggta tgaaaagatg cattttttca atgttcccga gcctgatgga   1080

catatcatat caccactgtt ggcaggattt tatatgtttt ggaccatgat cattttgtta   1140

caggtcttga ttcctatttc tctctatgtt tccatcgaaa ttgtgaagct tggacaaata   1200

tatttcattc aaagtgatgt ggatttctac aatgaaaaaa tggattctat tgttcagtgc   1260

cgagccctga acatcgccga ggatctggga cagattcagt acctcttttc cgataagaca   1320

ggaaccctca ctgagaataa gatggttttt cgaagatgta gtgtggcagg atttgattac   1380

tgccatgaag aaaatgccag gaggttggag tcctatcagg aagctgtctc tgaagatgaa   1440

gattttatag acacagtcag tggttccctc agcaatatgg caaaaccgag agcccccagc   1500

tgcaggacag ttcataatgg gcctttggga aataagccct caaatcatct tgctgggagc   1560

tcttttactc taggaagtgg agaaggagcc agtgaagtgc ctcattccag acaggctgct   1620

ttcagtagcc ccattgaaac agacgtggta ccagacacca ggcttttaga caaatttagt   1680
```

-continued

```
cagattacac ctcggctctt tatgccacta gatgagacca tccaaaatcc accaatggaa   1740
actttgtaca ttatcgactt tttcattgca ttggcaattt gcaacacagt agtggtttct   1800
gctcctaacc aaccccgaca aaagatcaga cacccttcac tgggggggtt gcccattaag   1860
tctttggaag agattaaaag tcttttccag agatggtctg tccgaagatc aagttctcca   1920
tcgcttaaca gtgggaaaga gccatcttct ggagttccaa acgcctttgt gagcagactc   1980
cctctcttta gtcgaatgaa accagcttca cctgtggagg aagaggtctc ccaggtgtgt   2040
gagagccccc agtgctccag tagctcagct tgctgcacag aaacagagaa acaacacggt   2100
gatgcaggcc tcctgaatgg caaggcagag tccctccctg gacagccatt ggcctgcaac   2160
ctgtgttatg aggccgagag cccagacgaa gcggccttag tgtatgccgc cagggcttac   2220
caatgcactt tacggtctcg gacaccagag caggtcatgg tggactttgc tgctttggga   2280
ccattaacat ttcaactcct acacatcctg ccctttgact cagtaagaaa aagaatgtct   2340
gttgtggtcc gacaccctct ttccaatcaa gttgtggtgt atacgaaagg cgctgattct   2400
gtgatcatgg agttactgtc ggtggcttcc ccagatggag caagtctgga gaaacaacag   2460
atgatagtaa gggagaaaac ccagaagcac ttggatgact atgccaaaca aggccttcgt   2520
actttatgta tagcaaagaa ggtcatgagt gacactgaat atgcagagtg gctgaggaat   2580
catttttag ctgaaaccag cattgacaac agggaagaat tactacttga atctgccatg    2640
aggttggaga acaaacttac attacttggt gctactggca ttgaagaccg tctgcaggag   2700
ggagtccctg aatctataga agctcttcac aaagcgggca tcaagatctg gatgctgaca   2760
ggggacaagc aggagacagc tgtcaacata gcttatgcat gcaaactact ggagccagat   2820
gacaagcttt ttatcctcaa tacccaaagt aaagatgcct gtgggatgct gatgagcaca   2880
attttgaaag aacttcagaa gaaaactcaa gccctgccag agcaagtgtc attaagtgaa   2940
gatttacttc agcctcctgt cccccgggac tcagggttac gagctggact cattatcact   3000
gggaagaccc tggagtttgc cctgcaagaa agtctgcaaa agcagttcct ggaactgaca   3060
tcttggtgtc aagctgtggt ctgctgccga gccacaccgc tgcagaaaag tgaagtggtg   3120
aaattggtcc gcagccatct ccaggtgatg acccttgcta ttggtgatgg tgccaatgat   3180
gttagcatga tacaagtggc agacattggg ataggggtct caggtcaaga aggcatgcag   3240
gctgtgatgg ccagtgactt tgccgtttct cagttcaaac atctcagcaa gctccttctt   3300
gtccatggac actggtgtta tacacggctt tccaacatga ttctctattt tttctataag   3360
aatgtggcct atgtgaacct ccttttctgg taccagttct tttgtggatt ttcaggaaca   3420
tccatgactg attactgggt tttgatcttc ttcaacctcc tcttcacatc tgcccctcct   3480
gtcatttatg gtgttttgga gaaagatgtg tctgcagaga ccctcatgca actgcctgaa   3540
ctttacagaa gtggtcagaa atcagaggca tacttacccc ataccttctg gatcacctta   3600
ttggatgctt tttatcaaag cctggtctgc ttctttgtgc cttattttac ctaccagggc   3660
tcagatactg acatctttgc atttggaaac cccctgaaca cagccactct gttcatcgtt   3720
ctcctccatc tggtcattga aagcaagagt ttgacttgga ttcacttgct ggtcatcatt   3780
ggtagcatct tgtcttattt tttatttgcc atagtttttg gagccatgtg tgtaacttgc   3840
aacccaccat ccaaccctta ctggattatg caggagcaca tgctggatcc agtattctac   3900
ttagtttgta tcctcacgac gtccattgct cttctgccca ggtttgtata cagagttctt   3960
cagggatccc tgtttccatc tccaattctg agagctaagc actttgacag actaactcca   4020
gaggagagga ctaaagctct caagaagtgg agaggggctg gaaagatgaa tcaagtgaca   4080
```

-continued tcaaagtatg ctaaccaatc agctggcaag tcaggaagaa gacccatgcc tggcccttct 4140
gctgtatttg caatgaagtc agcaacttcc tgtgctattg agcaaggaaa cttatctctg 4200
tgtgaaactg ctttagatca aggctactct gaaactaagg cctttgagat ggctggaccc 4260
tccaaaggta aagaaagcta g 4281

<210> SEQ ID NO 14
<211> LENGTH: 1426
<212> TYPE: PRT
<213> ORGANISM: homo sapiens

<400> SEQUENCE: 14

Met Thr Glu Ala Leu Gln Trp Ala Arg Tyr His Trp Arg Arg Leu Ile
1 5 10 15

Arg Gly Ala Thr Arg Asp Asp Asp Ser Gly Pro Tyr Asn Tyr Ser Ser
20 25 30

Leu Leu Ala Cys Gly Arg Lys Ser Ser Gln Ile Pro Lys Leu Ser Gly
35 40 45

Arg His Arg Ile Val Val Pro His Ile Gln Pro Phe Lys Asp Glu Tyr
50 55 60

Glu Lys Phe Ser Gly Ala Tyr Val Asn Asn Arg Ile Arg Thr Thr Lys
65 70 75 80

Tyr Thr Leu Leu Asn Phe Val Pro Arg Asn Leu Phe Glu Gln Phe His
85 90 95

Arg Ala Ala Asn Leu Tyr Phe Leu Phe Leu Val Val Leu Asn Trp Val
100 105 110

Pro Leu Val Glu Ala Phe Gln Lys Glu Ile Thr Met Leu Pro Leu Val
115 120 125

Val Val Leu Thr Ile Ile Ala Ile Lys Asp Gly Leu Glu Asp Tyr Arg
130 135 140

Lys Tyr Lys Ile Asp Lys Gln Ile Asn Asn Leu Ile Thr Lys Val Tyr
145 150 155 160

Ser Arg Lys Glu Lys Lys Tyr Ile Asp Arg Cys Trp Lys Asp Val Thr
165 170 175

Val Gly Asp Phe Ile Arg Leu Ser Cys Asn Glu Val Ile Pro Ala Asp
180 185 190

Met Val Leu Leu Phe Ser Thr Asp Pro Asp Gly Ile Cys His Ile Glu
195 200 205

Thr Ser Gly Leu Asp Gly Glu Ser Asn Leu Lys Gln Arg Gln Val Val
210 215 220

Arg Gly Tyr Ala Glu Gln Asp Ser Glu Val Asp Pro Glu Lys Phe Ser
225 230 235 240

Ser Arg Ile Glu Cys Glu Ser Pro Asn Asn Asp Leu Ser Arg Phe Arg
245 250 255

Gly Phe Leu Glu His Ser Asn Lys Glu Arg Val Gly Leu Ser Lys Glu
260 265 270

Asn Leu Leu Leu Arg Gly Cys Thr Ile Arg Asn Thr Glu Ala Val Val
275 280 285

Gly Ile Val Val Tyr Ala Gly His Glu Thr Lys Ala Met Leu Asn Asn
290 295 300

Ser Gly Pro Arg Tyr Lys Arg Ser Lys Leu Glu Arg Arg Ala Asn Thr
305 310 315 320

Asp Val Leu Trp Cys Val Met Leu Leu Val Ile Met Cys Leu Thr Gly
325 330 335

-continued

```
Ala Val Gly His Gly Ile Trp Leu Ser Arg Tyr Glu Lys Met His Phe
            340                 345                 350

Phe Asn Val Pro Glu Pro Asp Gly His Ile Ile Ser Pro Leu Leu Ala
        355                 360                 365

Gly Phe Tyr Met Phe Trp Thr Met Ile Ile Leu Leu Gln Val Leu Ile
    370                 375                 380

Pro Ile Ser Leu Tyr Val Ser Ile Glu Ile Val Lys Leu Gly Gln Ile
385                 390                 395                 400

Tyr Phe Ile Gln Ser Asp Val Asp Phe Tyr Asn Glu Lys Met Asp Ser
                405                 410                 415

Ile Val Gln Cys Arg Ala Leu Asn Ile Ala Glu Asp Leu Gly Gln Ile
            420                 425                 430

Gln Tyr Leu Phe Ser Asp Lys Thr Gly Thr Leu Thr Glu Asn Lys Met
        435                 440                 445

Val Phe Arg Arg Cys Ser Val Ala Gly Phe Asp Tyr Cys His Glu Glu
    450                 455                 460

Asn Ala Arg Arg Leu Glu Ser Tyr Gln Glu Ala Val Ser Glu Asp Glu
465                 470                 475                 480

Asp Phe Ile Asp Thr Val Ser Gly Ser Leu Ser Asn Met Ala Lys Pro
                485                 490                 495

Arg Ala Pro Ser Cys Arg Thr Val His Asn Gly Pro Leu Gly Asn Lys
            500                 505                 510

Pro Ser Asn His Leu Ala Gly Ser Ser Phe Thr Leu Gly Ser Gly Glu
        515                 520                 525

Gly Ala Ser Glu Val Pro His Ser Arg Gln Ala Ala Phe Ser Ser Pro
    530                 535                 540

Ile Glu Thr Asp Val Val Pro Asp Thr Arg Leu Leu Asp Lys Phe Ser
545                 550                 555                 560

Gln Ile Thr Pro Arg Leu Phe Met Pro Leu Asp Glu Thr Ile Gln Asn
                565                 570                 575

Pro Pro Met Glu Thr Leu Tyr Ile Ile Asp Phe Phe Ile Ala Leu Ala
            580                 585                 590

Ile Cys Asn Thr Val Val Val Ser Ala Pro Asn Gln Pro Arg Gln Lys
        595                 600                 605

Ile Arg His Pro Ser Leu Gly Gly Leu Pro Ile Lys Ser Leu Glu Glu
    610                 615                 620

Ile Lys Ser Leu Phe Gln Arg Trp Ser Val Arg Arg Ser Ser Ser Pro
625                 630                 635                 640

Ser Leu Asn Ser Gly Lys Glu Pro Ser Ser Gly Val Pro Asn Ala Phe
                645                 650                 655

Val Ser Arg Leu Pro Leu Phe Ser Arg Met Lys Pro Ala Ser Pro Val
            660                 665                 670

Glu Glu Glu Val Ser Gln Val Cys Glu Ser Pro Gln Cys Ser Ser Ser
        675                 680                 685

Ser Ala Cys Cys Thr Glu Thr Glu Lys Gln His Gly Asp Ala Gly Leu
    690                 695                 700

Leu Asn Gly Lys Ala Glu Ser Leu Pro Gly Gln Pro Leu Ala Cys Asn
705                 710                 715                 720

Leu Cys Tyr Glu Ala Glu Ser Pro Asp Glu Ala Ala Leu Val Tyr Ala
                725                 730                 735

Ala Arg Ala Tyr Gln Cys Thr Leu Arg Ser Arg Thr Pro Glu Gln Val
            740                 745                 750
```

-continued

Met Val Asp Phe Ala Ala Leu Gly Pro Leu Thr Phe Gln Leu Leu His
755 760 765

Ile Leu Pro Phe Asp Ser Val Arg Lys Arg Met Ser Val Val Val Arg
770 775 780

His Pro Leu Ser Asn Gln Val Val Val Tyr Thr Lys Gly Ala Asp Ser
785 790 795 800

Val Ile Met Glu Leu Leu Ser Val Ala Ser Pro Asp Gly Ala Ser Leu
805 810 815

Glu Lys Gln Gln Met Ile Val Arg Glu Lys Thr Gln Lys His Leu Asp
820 825 830

Asp Tyr Ala Lys Gln Gly Leu Arg Thr Leu Cys Ile Ala Lys Lys Val
835 840 845

Met Ser Asp Thr Glu Tyr Ala Glu Trp Leu Arg Asn His Phe Leu Ala
850 855 860

Glu Thr Ser Ile Asp Asn Arg Glu Glu Leu Leu Leu Glu Ser Ala Met
865 870 875 880

Arg Leu Glu Asn Lys Leu Thr Leu Leu Gly Ala Thr Gly Ile Glu Asp
885 890 895

Arg Leu Gln Glu Gly Val Pro Glu Ser Ile Glu Ala Leu His Lys Ala
900 905 910

Gly Ile Lys Ile Trp Met Leu Thr Gly Asp Lys Gln Glu Thr Ala Val
915 920 925

Asn Ile Ala Tyr Ala Cys Lys Leu Leu Glu Pro Asp Asp Lys Leu Phe
930 935 940

Ile Leu Asn Thr Gln Ser Lys Asp Ala Cys Gly Met Leu Met Ser Thr
945 950 955 960

Ile Leu Lys Glu Leu Gln Lys Lys Thr Gln Ala Leu Pro Glu Gln Val
965 970 975

Ser Leu Ser Glu Asp Leu Leu Gln Pro Pro Val Pro Arg Asp Ser Gly
980 985 990

Leu Arg Ala Gly Leu Ile Ile Thr Gly Lys Thr Leu Glu Phe Ala Leu
995 1000 1005

Gln Glu Ser Leu Gln Lys Gln Phe Leu Glu Leu Thr Ser Trp Cys Gln
1010 1015 1020

Ala Val Val Cys Cys Arg Ala Thr Pro Leu Gln Lys Ser Glu Val Val
1025 1030 1035 1040

Lys Leu Val Arg Ser His Leu Gln Val Met Thr Leu Ala Ile Gly Asp
1045 1050 1055

Gly Ala Asn Asp Val Ser Met Ile Gln Val Ala Asp Ile Gly Ile Gly
1060 1065 1070

Val Ser Gly Gln Glu Gly Met Gln Ala Val Met Ala Ser Asp Phe Ala
1075 1080 1085

Val Ser Gln Phe Lys His Leu Ser Lys Leu Leu Leu Val His Gly His
1090 1095 1100

Trp Cys Tyr Thr Arg Leu Ser Asn Met Ile Leu Tyr Phe Phe Tyr Lys
1105 1110 1115 1120

Asn Val Ala Tyr Val Asn Leu Leu Phe Trp Tyr Gln Phe Phe Cys Gly
1125 1130 1135

Phe Ser Gly Thr Ser Met Thr Asp Tyr Trp Val Leu Ile Phe Phe Asn
1140 1145 1150

Leu Leu Phe Thr Ser Ala Pro Pro Val Ile Tyr Gly Val Leu Glu Lys
1155 1160 1165

-continued

```
Asp Val Ser Ala Glu Thr Leu Met Gln Leu Pro Glu Leu Tyr Arg Ser
    1170                1175                1180

Gly Gln Lys Ser Glu Ala Tyr Leu Pro His Thr Phe Trp Ile Thr Leu
1185                1190                1195                1200

Leu Asp Ala Phe Tyr Gln Ser Leu Val Cys Phe Phe Val Pro Tyr Phe
                1205                1210                1215

Thr Tyr Gln Gly Ser Asp Thr Asp Ile Phe Ala Phe Gly Asn Pro Leu
            1220                1225                1230

Asn Thr Ala Thr Leu Phe Ile Val Leu Leu His Leu Val Ile Glu Ser
        1235                1240                1245

Lys Ser Leu Thr Trp Ile His Leu Leu Val Ile Ile Gly Ser Ile Leu
    1250                1255                1260

Ser Tyr Phe Leu Phe Ala Ile Val Phe Gly Ala Met Cys Val Thr Cys
1265                1270                1275                1280

Asn Pro Pro Ser Asn Pro Tyr Trp Ile Met Gln Glu His Met Leu Asp
                1285                1290                1295

Pro Val Phe Tyr Leu Val Cys Ile Leu Thr Thr Ser Ile Ala Leu Leu
            1300                1305                1310

Pro Arg Phe Val Tyr Arg Val Leu Gln Gly Ser Leu Phe Pro Ser Pro
        1315                1320                1325

Ile Leu Arg Ala Lys His Phe Asp Arg Leu Thr Pro Glu Glu Arg Thr
    1330                1335                1340

Lys Ala Leu Lys Lys Trp Arg Gly Ala Gly Lys Met Asn Gln Val Thr
1345                1350                1355                1360

Ser Lys Tyr Ala Asn Gln Ser Ala Gly Lys Ser Gly Arg Arg Pro Met
                1365                1370                1375

Pro Gly Pro Ser Ala Val Phe Ala Met Lys Ser Ala Thr Ser Cys Ala
            1380                1385                1390

Ile Glu Gln Gly Asn Leu Ser Leu Cys Glu Thr Ala Leu Asp Gln Gly
        1395                1400                1405

Tyr Ser Glu Thr Lys Ala Phe Glu Met Ala Gly Pro Ser Lys Gly Lys
    1410                1415                1420

Glu Ser
1425
```

<210> SEQ ID NO 15
<211> LENGTH: 1737
<212> TYPE: DNA
<213> ORGANISM: homo sapiens

<400> SEQUENCE: 15

```
atgagtgaca ctgaatatgc agagtggctg aggaatcatt ttttagctga aaccagcatt      60

gacaacaggg aagaattact acttgaatct gccatgaggt tggagaacaa acttacatta     120

cttggtgcta ctggcattga agaccgtctg caggagggag tccctgaatc tatagaagct     180

cttcacaaag cgggcatcaa gatctggatg ctgacagggg acaagcagga gacagctgtc     240

aacatagctt atgcatgcaa actactggag ccagatgaca agctttttat cctcaatacc     300

caaagtaaag atgcctgtgg gatgctgatg agcacaattt tgaaagaact tcagaagaaa     360

actcaagccc tgccagagca agtgtcatta agtgaagatt tacttcagcc tcctgtcccc     420

cgggactcag ggttacgagc tggactcatt atcactggga agaccctgga gtttgccctg     480

caagaaagtc tgcaaaagca gttcctggaa ctgacatctt ggtgtcaagc tgtggtctgc     540

tgccgagcca caccgctgca gaaaagtgaa gtggtgaaat tggtccgcag ccatctccag     600
```

-continued

```
gtgatgaccc ttgctattgg tgatggtgcc aatgatgtta gcatgataca agtggcagac    660

attgggatag gggtctcagg tcaagaaggc atgcaggctg tgatggccag tgactttgcc    720

gtttctcagt tcaaacatct cagcaagctc cttcttgtcc atggacactg gtgttataca    780

cggctttcca acatgattct ctatttttc tataagaatg tggcctatgt gaacctcctt    840

ttctggtacc agttcttttg tggattttca ggaacatcca tgactgatta ctgggttttg    900

atcttcttca acctcctctt cacatctgcc cctcctgtca tttatggtgt tttggagaaa    960

gatgtgtctg cagagaccct catgcaactg cctgaacttt acagaagtgg tcagaaatca   1020

gaggcatact taccccatac cttctggatc accttattgg atgcttttta tcaaagcctg   1080

gtctgcttct ttgtgcctta ttttacctac cagggctcag atactgacat ctttgcattt   1140

ggaaaccccc tgaacacagc cactctgttc atcgttctcc tccatctggt cattgaaagc   1200

aagagtttga cttggattca cttgctggtc atcattggta gcatcttgtc ttattttta   1260

tttgccatag tttttggagc catgtgtgta acttgcaacc caccatccaa cccttactgg   1320

attatgcagg agcacatgct ggatccagta ttctacttag tttgtatcct cacgacgtcc   1380

attgctcttc tgcccaggtt tgtatacaga gttcttcagg gatccctgtt tccatctcca   1440

attctgagag ctaagcactt tgacagacta actccagagg agaggactaa agctctcaag   1500

aagtggagag ggctggaaa gatgaatcaa gtgacatcaa agtatgctaa ccaatcagct   1560

ggcaagtcag gaagaagacc catgcctggc ccttctgctg tatttgcaat gaagtcagca   1620

acttcctgtg ctattgagca aggaaactta tctctgtgtg aaactgcttt agatcaaggc   1680

tactctgaaa ctaaggcctt tgagatggct ggaccctcca aaggtaaaga aagctag      1737
```

<210> SEQ ID NO 16
<211> LENGTH: 578
<212> TYPE: PRT
<213> ORGANISM: homo sapiens

<400> SEQUENCE: 16

```
Met Ser Asp Thr Glu Tyr Ala Glu Trp Leu Arg Asn His Phe Leu Ala
 1               5                  10                  15

Glu Thr Ser Ile Asp Asn Arg Glu Glu Leu Leu Leu Glu Ser Ala Met
            20                  25                  30

Arg Leu Glu Asn Lys Leu Thr Leu Leu Gly Ala Thr Gly Ile Glu Asp
        35                  40                  45

Arg Leu Gln Glu Gly Val Pro Glu Ser Ile Glu Ala Leu His Lys Ala
    50                  55                  60

Gly Ile Lys Ile Trp Met Leu Thr Gly Asp Lys Gln Glu Thr Ala Val
65                  70                  75                  80

Asn Ile Ala Tyr Ala Cys Lys Leu Leu Glu Pro Asp Asp Lys Leu Phe
                85                  90                  95

Ile Leu Asn Thr Gln Ser Lys Asp Ala Cys Gly Met Leu Met Ser Thr
            100                 105                 110

Ile Leu Lys Glu Leu Gln Lys Lys Thr Gln Ala Leu Pro Glu Gln Val
        115                 120                 125

Ser Leu Ser Glu Asp Leu Leu Gln Pro Pro Val Pro Arg Asp Ser Gly
    130                 135                 140

Leu Arg Ala Gly Leu Ile Ile Thr Gly Lys Thr Leu Glu Phe Ala Leu
145                 150                 155                 160

Gln Glu Ser Leu Gln Lys Gln Phe Leu Glu Leu Thr Ser Trp Cys Gln
                165                 170                 175
```

-continued

```
Ala Val Val Cys Cys Arg Ala Thr Pro Leu Gln Lys Ser Glu Val Val
            180                 185                 190

Lys Leu Val Arg Ser His Leu Gln Val Met Thr Leu Ala Ile Gly Asp
        195                 200                 205

Gly Ala Asn Asp Val Ser Met Ile Gln Val Ala Asp Ile Gly Ile Gly
    210                 215                 220

Val Ser Gly Gln Glu Gly Met Gln Ala Val Met Ala Ser Asp Phe Ala
225                 230                 235                 240

Val Ser Gln Phe Lys His Leu Ser Lys Leu Leu Leu Val His Gly His
                245                 250                 255

Trp Cys Tyr Thr Arg Leu Ser Asn Met Ile Leu Tyr Phe Phe Tyr Lys
            260                 265                 270

Asn Val Ala Tyr Val Asn Leu Leu Phe Trp Tyr Gln Phe Phe Cys Gly
        275                 280                 285

Phe Ser Gly Thr Ser Met Thr Asp Tyr Trp Val Leu Ile Phe Phe Asn
    290                 295                 300

Leu Leu Phe Thr Ser Ala Pro Pro Val Ile Tyr Gly Val Leu Glu Lys
305                 310                 315                 320

Asp Val Ser Ala Glu Thr Leu Met Gln Leu Pro Glu Leu Tyr Arg Ser
                325                 330                 335

Gly Gln Lys Ser Glu Ala Tyr Leu Pro His Thr Phe Trp Ile Thr Leu
            340                 345                 350

Leu Asp Ala Phe Tyr Gln Ser Leu Val Cys Phe Phe Val Pro Tyr Phe
        355                 360                 365

Thr Tyr Gln Gly Ser Asp Thr Asp Ile Phe Ala Phe Gly Asn Pro Leu
    370                 375                 380

Asn Thr Ala Thr Leu Phe Ile Val Leu Leu His Leu Val Ile Glu Ser
385                 390                 395                 400

Lys Ser Leu Thr Trp Ile His Leu Leu Val Ile Ile Gly Ser Ile Leu
                405                 410                 415

Ser Tyr Phe Leu Phe Ala Ile Val Phe Gly Ala Met Cys Val Thr Cys
            420                 425                 430

Asn Pro Pro Ser Asn Pro Tyr Trp Ile Met Gln Glu His Met Leu Asp
        435                 440                 445

Pro Val Phe Tyr Leu Val Cys Ile Leu Thr Thr Ser Ile Ala Leu Leu
    450                 455                 460

Pro Arg Phe Val Tyr Arg Val Leu Gln Gly Ser Leu Phe Pro Ser Pro
465                 470                 475                 480

Ile Leu Arg Ala Lys His Phe Asp Arg Leu Thr Pro Glu Glu Arg Thr
                485                 490                 495

Lys Ala Leu Lys Lys Trp Arg Gly Ala Gly Lys Met Asn Gln Val Thr
            500                 505                 510

Ser Lys Tyr Ala Asn Gln Ser Ala Gly Lys Ser Gly Arg Arg Pro Met
        515                 520                 525

Pro Gly Pro Ser Ala Val Phe Ala Met Lys Ser Ala Thr Ser Cys Ala
    530                 535                 540

Ile Glu Gln Gly Asn Leu Ser Leu Cys Glu Thr Ala Leu Asp Gln Gly
545                 550                 555                 560

Tyr Ser Glu Thr Lys Ala Phe Glu Met Ala Gly Pro Ser Lys Gly Lys
                565                 570                 575

Glu Ser
```

-continued

<210> SEQ ID NO 17
<211> LENGTH: 5958
<212> TYPE: DNA
<213> ORGANISM: homo sapiens

<400> SEQUENCE: 17
gtcagctaca caacctggat cttaccacag tttggatatg actgaggctc tccaatgggc 60
cagatatcac tggcgacggc tgatcagagg tgcaaccagg gatgatgatt cagggccata 120
caactattcc tcgttgctcg cctgtgggcg caagtcctct cagatcccta aactgtcagg 180
aaggcaccgg attgttgttc cccacatcca gcccttcaag gatgagtatg agaagttctc 240
cggagcctat gtgaacaatc gaatacgaac aacaaagtac acacttctga attttgtgcc 300
aagaaattta tttgaacaat ttcacagagc tgccaattta tatttcctgt tcctagttgt 360
cctgaactgg gtacctttgg tagaagcctt ccaaaaggaa atcaccatgt tgcctctggt 420
ggtggtcctt acaattatcg caattaaaga tggcctggaa gattatcgga aatacaaaat 480
tgacaaacag atcaataatt taataactaa agtttatagt aggaaagaga aaaaatacat 540
tgaccgatgc tggaaagacg ttactgttgg ggactttatt cgcctctcct gcaacgaggt 600
catccctgca gacatggtac tactcttttc cactgatcca gatggaatct gtcacattga 660
gacttctggt cttgatggag agagcaattt aaaacagagg caggtggttc ggggatatgc 720
agaacaggac tctgaagttg atcctgagaa gttttccagt aggatagaat gtgaaagccc 780
aaacaatgac ctcagcagat tccgaggctt cctagaacat tccaacaaag aacgcgtggg 840
tctcagtaaa gaaaatttgt tgcttagagg atgcaccatt agaaacacag aggctgttgt 900
gggcattgtg gtttatgcag gccatgaaac caaagcaatg ctgaacaaca gtgggccacg 960
gtataagcgc agcaaattag aaagaagagc aaacacagat gtcctctggt gtgtcatgct 1020
tctggtcata atgtgcttaa ctggcgcagt aggtcatgga atctggctga gcaggtatga 1080
aaagatgcat tttttcaatg ttcccgagcc tgatggacat atcatatcac cactgttggc 1140
aggattttat atgttttgga ccatgatcat tttgttacag gtcttgattc ctatttctct 1200
ctatgtttcc atcgaaattg tgaagcttgg acaaatatat ttcattcaaa gtgatgtgga 1260
tttctacaat gaaaaaatgg attctattgt tcagtgccga gccctgaaca tcgccgagga 1320
tctgggacag attcagtacc tcttttccga taagacagga accctcactg agaataagat 1380
ggtttttcga agatgtagtg tggcaggatt tgattactgc catgaagaaa atgccaggag 1440
gttggagtcc tatcaggaag ctgtctctga agatgaagat tttatagaca cagtcagtgg 1500
ttccctcagc aatatggcaa aaccgagagc ccccagctgc aggacagttc ataatgggcc 1560
tttgggaaat aagccctcaa atcatcttgc tgggagctct tttactctag gaagtggaga 1620
aggagccagt gaagtgcctc attccagaca ggctgctttc agtagcccca ttgaaacaga 1680
cgtggtacca gacaccaggc ttttagacaa atttagtcag attacacctc ggctctttat 1740
gccactagat gagaccatcc aaaatccacc aatggaaact ttgtacatta tcgacttttt 1800
cattgcattg gcaatttgca acacagtagt ggtttctgct cctaaccaac cccgacaaaa 1860
gatcagacac ccttcactgg gggggttgcc cattaagtct ttggaagaga ttaaaagtct 1920
tttccagaga tggtctgtcc gaagatcaag ttctccatcg cttaacagtg ggaaagagcc 1980
atcttctgga gttccaaacg cctttgtgag cagactccct ctctttagtc gaatgaaacc 2040
agcttcacct gtggaggaag aggtctccca ggtgtgtgag agcccccagt gctccagtag 2100
ctcagcttgc tgcacagaaa cagagaaaca acacggtgat gcaggcctcc tgaatggcaa 2160

-continued

```
ggcagagtcc ctccctggac agccattggc ctgcaacctg tgttatgagg ccgagagccc   2220
agacgaagcg gccttagtgt atgccgccag ggcttaccaa tgcactttac ggtctcggac   2280
accagagcag gtcatggtgg actttgctgc tttgggacca ttaacatttc aactcctaca   2340
catcctgccc tttgactcag taagaaaaag aatgtctgtt gtggtccgac accctctttc   2400
caatcaagtt gtggtgtata cgaaaggcgc tgattctgtg atcatggagt tactgtcggt   2460
ggcttcccca gatggagcaa gtctggagaa acaacagatg atagtaaggg agaaaaccca   2520
gaagcacttt tttcttccat ttcaggtgtc gtgaaaagct tgaattcggc gcgccagata   2580
tcacgcgtgc caagggactg gctcaggatg actatgccaa acaaggcctt cgtactttat   2640
gtatagcaaa gaaggtcatg agtgacactg aatatgcaga gtggctgagg aatcattttt   2700
tagctgaaac cagcattgac aacagggaag aattactact tgaatctgcc atgaggttgg   2760
agaacaaact tacattactt ggtgctactg gcattgaaga ccgtctgcag gagggagtcc   2820
ctgaatctat agaagctctt cacaaagcgg gcatcaagat ctggatgctg acaggggaca   2880
agcaggagac agctgtcaac atagcttatg catgcaaact actggagcca gatgacaagc   2940
tttttatcct caatacccaa agtaaagtgc gtatattgag attaaatctg ttcttctgta   3000
ttttcaaagg cattggaaca tttgagattt gatgtatgca aggattaaaa aaatgcctgt   3060
gggatgctga tgagcacaat tttgaaagaa cttcagaaga aaactcaagc cctgccagag   3120
caagtgtcat taagtgaaga tttacttcag cctcctgtcc cccgggactc agggttacga   3180
gctggactca ttatcactgg gaagaccctg gagtttgccc tgcaagaaag tctgcaaaag   3240
cagttcctgg aactgacatc ttggtgtcaa gctgtggtct gctgccgagc cacaccgctg   3300
cagaaaagtg aagtggtgaa attggtccgc agccatctcc aggtgatgac ccttgctatt   3360
ggtgagtgag gatgaatctg agtcctgctc ttctcccttt cacaccacac cagacaccga   3420
tccttctgtc tctttcttct cccactgttc cttccatttt cctcctccct ttttctctac   3480
cacattcatg ccttcccatc acctatttga gcaccttcct ccatcaccta tttgagcacc   3540
ttctgtgaac caggtaatag ggatgtgaca tggtaaacaa tacagtagtc cagacttctt   3600
agttcagtgt cagaccccca aatcaacaag cttaaatcaa gtaataaact gaatcacaga   3660
actgaaaaat ccatgtgttc taccttcagg aaagctaaat tcaaggacat gagaattcat   3720
ttctttatcc attccacaag tatttatcaa gtgccttttt tgtaccaggc atttttctag   3780
atggagatac aagagtatat aaaattggca aactaccttt ttacaaggaa cttacatcta   3840
gtaggaaggc atgcagttaa acaaagcata atctgtcagg ttcaggtagt gataagtact   3900
attggaaaaa taagtggatg aggacacgta tagcactgga gatgggctgg ggctgctctt   3960
taaatcgatt tcaagagcta ctgtaagttg actgggagca gagatgtgaa ggaaatcata   4020
aggggccatg gagacatggt ggtgccaatg atgttagcat gatacaagtg gcagacattg   4080
ggatagggt ctcaggtcaa gaaggcatgc aggctgtgat ggccagtgac tttgccgttt   4140
ctcagttcaa acatctcagc aagctccttc ttgtccatgg acactggtgt tatacacggc   4200
tttccaacat gattctctat tttttctata agaatgtggc ctatgtgaac ctccttttct   4260
ggtaccagtt cttttgtgga ttttcaggaa catccatgac tgattactgg gttttgatct   4320
tcttcaacct cctcttcaca tctgcccctc ctgtcattta tggtgttttg gagaaagatg   4380
tgtctgcaga gaccctcatg caactgcctg aactttacag aagtggtcag aaatcagagg   4440
catacttacc ccataccttc tggatcacct tattggatgc tttttatcaa agcctggtct   4500
gcttctttgt gccttatttt acctaccagg gctcagatac tgacatcttt gcatttggaa   4560
```

-continued

| | |
|---|---|
| acccoctgaa cacagccact ctgttcatcg ttctcctcca tctggtcatt gaaagcaaga | 4620 |
| gtttgaccag gtgcagtgac tcacacctgc aattccagag ctttgggagg ctgtggatca | 4680 |
| catgaagcta agagttcaag accagcctgg gcaacataac ttggattcac ttgctggtca | 4740 |
| tcattggtag catcttgtct tattttttat ttgccatagt ttttggagcc atgtgtgtaa | 4800 |
| cttgcaaccc accatccaac ccttactgga ttatgcagga gcacatgctg gatccagtat | 4860 |
| tctacttagt ttgtatcctc acgacgtcca ttgctcttct gcccaggttt gtatacagag | 4920 |
| ttcttcaggg atccctgttt ccatctccaa ttctgagagc taagcacttt gacagactaa | 4980 |
| ctccagagga gaggactaaa gctctcaaga agtggagagg ggctggaaag atgaatcaag | 5040 |
| tgacatcaaa gtatgctaac caatcagctg gcaagtcagg aagaagaccc atgcctggcc | 5100 |
| cttctgctgt atttgcaatg aagtcagcaa cttcctgtgc tattgagcaa ggaaacttat | 5160 |
| ctctgtgtga aactgcttta gatcaaggct actctgaaac taaggccttt gagatggctg | 5220 |
| gaccctccaa aggtaaagaa agctagatac cctccttgga gttgcaagta ttctttcaag | 5280 |
| gttggaagag ggattttgaa gaggtatctc tccaagcaag aatgacttgt ttttccataa | 5340 |
| gggacatgag cattttacta ggcttggaag agctgacatg atgagcatta ttgtatgttt | 5400 |
| gtatatacat ttgtgataga gggctagagt ttgacctaga gagagtttaa ggaagtgaaa | 5460 |
| tatttaattc agaaccaaat gcttttgtaa aacttttttgg attttgtaaa agcattttca | 5520 |
| ttctcttaga aattcaagta ttttcaaggg gagtcatttg agatatattt attttactag | 5580 |
| gagatcttat attctaggga aatgctttaa atggtcaggc tccaatcgga attttttttaa | 5640 |
| gaaaaaagta gtttttaata cattggttag gactcagagg aaatacggaa aaaacattgt | 5700 |
| agatggtaat ttacagataa aatcccaaga gcctttaaac aacaaggtac ctaaataggg | 5760 |
| tataattata ctgcttaaaa tacaggtagt gcctattaat agctttttat ttcctatggg | 5820 |
| gagatgcttt ggtcttctgg ctgagatgta ggcatacctc tcactcattt caatgctttc | 5880 |
| ctgaggtgga gccttcattg gaaaggggaa agagggttct aggttcatca gggaccagga | 5940 |
| atgctttcct ctggcagg | 5958 |